United States Patent
Catalano et al.

(10) Patent No.: US 8,999,718 B2
(45) Date of Patent: Apr. 7, 2015

(54) VAPOCHROMIC MATERIALS AND METHODS OF MAKING AND USING SAME

(75) Inventors: Vincent J. Catalano, Reno, NV (US); Christoph E. Strasser, Dottikon (CH)

(73) Assignee: Board of Regents of the Nevada System of Higher Education, on behalf of the University of Nevada, Reno, Reno, NV (US)

( * ) Notice: Subject to any disclaimer, the term of this patent is extended or adjusted under 35 U.S.C. 154(b) by 268 days.

(21) Appl. No.: 13/537,396

(22) Filed: Jun. 29, 2012

(65) Prior Publication Data

US 2013/0011926 A1 Jan. 10, 2013

Related U.S. Application Data

(60) Provisional application No. 61/502,569, filed on Jun. 29, 2011.

(51) Int. Cl.
*G01N 33/00* (2006.01)
*C07F 1/08* (2006.01)
*C07F 1/12* (2006.01)
*G01N 21/77* (2006.01)

(52) U.S. Cl.
CPC ... *C07F 1/08* (2013.01); *C07F 1/12* (2013.01); *G01N 2021/7786* (2013.01)

(58) Field of Classification Search
None
See application file for complete search history.

(56) References Cited

U.S. PATENT DOCUMENTS

| | | |
|---|---|---|
| 5,766,952 A | 6/1998 | Mann et al. |
| 2004/0138456 A1 | 7/2004 | Kato |
| 2008/0071053 A1 | 3/2008 | Lefebvre et al. |
| 2009/0130768 A1 | 5/2009 | Lefebvre et al. |

FOREIGN PATENT DOCUMENTS

WO 2010031485 A1 3/2010

OTHER PUBLICATIONS

Espacenet, EPO English Machine Translation of Application No. WO 2010/031485 (A1), Published Mar. 25, 2010, http://worldwide.espacenet.com, retrieved Jan. 11, 2013, 14 pp.

Bariain et al., "Optical fibre sensors based on vapochromic gold complexes for environmental applications," Sensors and Actuators B. 108:535-541, 2005.

Beauvais et al., "Cyano-Bridged Re6Q8 (Q = S, Se) Cluster-Cobalt(II) Framework Materials: Versatile Solid Chemical Sensors," J. Am. Chem. Soc. 122:2763-2772, 2000.

(Continued)

*Primary Examiner* — Robert Xu
(74) *Attorney, Agent, or Firm* — Klarquist Sparkman, LLP

(57) ABSTRACT

A vapochromic gold-copper complex $[AuL_2(Cu(Y)_n)_2](X)_3$ exhibiting luminescence is provided, where L is an N-heterocyclic carbene; Y is a heteroatom-containing ligand; X is an anion, and n is an integer having a value of 1 or 2, and solvates thereof. A reaction of $[AuL_2(Cu(Y)_n)_2](X)_3$ with water vapor or an organic compound vapor, for example, affords a modified complex that yields a change in luminescence color under UV excitation. These tricationic vapochromic materials exhibit large changes in the emission through ligand substitution reactions between the solid complex and vapors, which permit use in luminescent vapochromic sensors.

23 Claims, 11 Drawing Sheets

(56) References Cited

OTHER PUBLICATIONS

Bradshaw et al., "Reversible Concerted Ligand Substitution at Alternating Metal Sites in an Extended Solid," Science. 315:977-980, 2007.

Burks et al., "Current trends in the detection of peroxide-based explosives," Anal Bioanal Chem. 395:301-313, 2009.

Buss et al., "Structural Investigations of Vapochromic Behavior. X-ray Single-Crystal and Powder Diffraction Studies of [Pt(CN-iso-C3H7)4][M(CN)4] for M = Pt or Pd," J. Am. Chem. Soc. 120:7783-7790, 1998.

Buss et al., "Synthesis and Characterization of Pt(Cn-p-(C2H5)C6H4)2, a Crystalline Vapoluminescent Compound That Detects Vapor-Phase Aromatic Hydrocarbons," J. Am. Chem. Soc. 124(6):1031-1039, 2002.

Calhorda et al., "Heteropolynuclear Gold Complexes with Metallophilic Interactions: Modulation of the Luminescent Properties," Inorg. Chem. 49:8255-8269, 2010.

Cariati et al., "Luminescence response of the solid state polynuclear copper(I) iodide materials [CuI(4-picoline)]x to volatile organic compounds," Chem. Commun. pp. 1623-1624, 1998.

Cariati et al., "Solvent- and Vapor-Induced Isomerization between the Luminescent Solids [CuI(4-pic)]4 and [CuI(4-pic)]∞ (pic = methylpyridine). The Structural Basis for the Observed Luminescence Vapochromism," Chem. Mater. 12:3385-3391, 2000.

Catalano et al., "Luminescent Copper(I) Halide Butterfly Dimers Coordinated to [Au(CH3imCH2py)2]BF4 and [Au(CH3imCH2quin)2]BF4," Inorg. Chem. 48:11362-11375, 2009.

Catalano et al., "Mono-, Di-, and Trinuclear Luminescent Silver(I) and Gold(I) N-Heterocyclic Carbene Complexes Derived from the Picolyl-Substituted Methylimidazolium Salt: 1-Methyl-3-(2-pyridinylmethyl)-1H-imidazolium Tetrafluoroborate," Inorg. Chem. 44(19):6558-6566, 2005.

Daws et al., "Vapochromic Compounds as Environmental Sensors. 2. Synthesis and Near-Infrared and Infrared Spectroscopy Studies of [Pt(arylisocyanide)4][Pt(CN)4] upon Exposure to Volatile Organic Compound Vapors," Chem. Mater. 9:363-368, 1997.

Drew et al., "A Platinum(II) Extended Linear Chain Material That Selectively Uptakes Benzene," Chem. Mater. 21:3117-3124, 2009.

Du, P., "A highly selective vapochromic methanol sensor based on one step synthesis of a simple platinum terpyridine complex," Inorganica Chimica Acta. 363:1355-1358, 2010.

Du et al., "Synthesis and Structural Characterization of a New Vapochromic Pt(II) Complex Based on the 1-Terpyridyl-2,3,4,5,6-pentaphenylbenzene (TPPPB) Ligand," Inorg. Chem. 47:69-77, 2008.

Elosua et al., "Detection of Volatile Organic Compounds Based on Optical Fibre Using Nanostructured Films," International Journal on Smart Sensing and Intelligent Systems. 1(1): 123-136, 2008.

Elosua et al., "Optical fiber sensing devices based on organic vapor indicators towards sensor array implementation," Sensors and Actuators B. 137:139-146, 2009.

Espallargas et al., "Reversible Extrusion and Uptake of HCl Molecules by Crystalline Solids Involving Coordination Bond Cleavage and Formation," J. Am. Chem. Soc. 128: 9584-9585, 2006.

Espallargas et al., "Reversible Gas Uptake by a Nonporous Crystalline Solid Involving Multiple Changes in Covalent Bonding," J. Am. Chem. Soc. 129:15606-15614, 2007.

Exstrom et al., "Inclusion of Organic Vapors by Crystalline, Solvatochromic [Pt(aryl isonitrile)4][Pd(CN)4] Compounds. 'Vapochromic' Environmental Sensors," Chem. Mater 7:15-17, 1995.

Fernández et al., "A Detailed Study of the Vapochromic Behavior of {Tl[Au(C6Cl5)2]}n," Inorg. Chem. 43:3573-3581, 2004.

Fernández et al., "{Tl[Au(C6Cl5)2]}n: A Vapochromic Complex," J. Am. Chem. Soc. 125:2022-2023, 2003.

Fernández et al., "Gold-heterometal complexes. Evolution of a new class of luminescent materials," Dalton Trans. pp. 1969-1981, 2007.

Fernández et al., "Photophysical and Theoretical Studies on Luminescent Tetranuclear Coinage Metal Building Blocks," Organometallics. 25:3639-3646, 2006.

Fernández et al., "Unsupported Au(I)—Cu(I) interactions: influence of nitrile ligands and aurophilicity on the structure and luminescence," Dalton Trans. pp. 7509-7518, 2009.

Fernández et al., "Unsupported Gold(I)—Copper(I) Interactions through η1Au-[AU(C6F5)2]—Coordination to Cu+ Lewis Acid Sites," Inorg. Chem. 44:1163-1165, 2005.

Fernández et al., "Vapochromic Behavior of {Ag2(Et2O)2[Au(C6F5)2]2}n with Volatile Organic Compounds," Inorg. Chem. 47:8069-8076, 2008.

Ghosh et al., "Synthesis and Characterization of a Series of New Luminescent NHC-Coordinated AuI-AgI Tetra- and Polymetallic Complexes Containing Benzoate-Bridged Ag2 Dimers," Eur. J. Inorg. Chem. pp. 1832-1843, 2009.

Grove et al., "A New Class of Platinum(II) Vapochromic Salts," J. Am. Chem. Soc. 126:1594-1595, 2004.

Hao et al., "A Gold(I) Mononuclear Complex and Its Association into Binuclear and Cluster Compounds by Hydrogen Bonding or Metal Ion Coordination," Inorg. Chem. 39:5520-5529, 2000.

He et al., "Design and Synthesis of Calixarene-Based Bis-alkynyl-Bridged Dinuclear AuI Isonitrile Complexes as Luniescent Ion Probes by the Modulation of Au—Au Interactions," Chem. Eur. J. 15:8842-8851, 2009.

Kato et al., "Vapor-Induced Luminescence Switching in Crystals of the Syn Isomer of a Dinuclear (Bipyridine) platinum(II) Complex Bridged with Pyridine-2-Thiolate Ions," Angnew. Chem. Int. Ed. 41(17):3183-3185, 2002.

Kawata et al., "Metal-Complex Assemblies Constructed from the Flexible Hinge-Like Ligand H2bhnq: Structural Versatility and Dynamic Behavior in the Solid State," Chem. Eur. J. 10:2647-2660, 2004.

Kinayyigit, Solen, Platinum(II) Change Transfer Chromophores: Electrochemistry, Photophysics, and Vapochromic Sensing Applications, Bowling Green State University, 2007, 186 pp.

Kojima et al., "Tetradentate Schiff base-oxovanadium(IV) complexes: structures and reactivities in the solid state," Coordination Chemistry Reviews. 237:183-196, 2003.

Koshevoy et al., "Supramolecular Luminescent Gold(I)—Copper(I) Complexes: Self-Assembly of the AuxCuy Clusters inside the [Au3(diphosphine)3]3+ Triangles," Inorg. Chem. 47:9478-9488, 2008.

Kui et al., "Structures, Photoluminescence, and Reversible Vapoluminescence Properties of Neutral Platinum(II) Complexes Containing Extended π-Conjugated Cyclometalated Ligands," J. Am. Chem. Soc. 128:8297-8309, 2006.

Laguna et al., "Combining Aurophilic Interactions and Halogen Bonding To Control the Luminescence from Bimetallic Gold-Silver Clusters," J. Am. Chem. Soc. 132:456-457, 2010.

Lefebvre et al., "Cu[Au(CN)2]2(DMSO)2: Golden Polymorphs That Exhibit Vapochromic Behavior," J. Am. Chem. Soc. 126:16117-16125, 2004.

Lennartson et al., "cis- and trans-Bis(benzoylacetonato)pyridinecopper(II): co-crystallisation of isomers and reversible pyridine loss with retention of crystallinity," New J. Chem. 31:344-347, 2007.

Liu et al., "Acetonitrile-Vapor-Induced Color and Luminescence Changes in a Cyclometalated Heteroleptic Iridium Complex," Inorg. Chem. 47:8025-8030, 2008.

Lu et al., "π-π Interactions in Organometallic Systems. Crystal Structures and Spectroscopic Properties of Luminescent Mono-, Bi-, and Trinuclear Trans-cyclometalated Platinum(II) Complexes Derived from 2,6-Diphenyldyridine," Organometallics. 20:2477-2486, 2001.

Lu et al., "Structural Basis for Vapoluminescent Organoplatinum Materials Derived from Noncovalent Interactions as Recognition Components," Chem. Eur. J. 9:6155-6166, 2003.

Luquin et al., "Application of Gold Complexes in the Development of Sensors for Volatile Organic Compounds," Gold Bulletin. 40(3):225-233, 2007.

Manbeck et al., "Luminescent Au(I)/Cu(I) Alkynyl Clusters with an Ethynyl Steroid and Related Aliphatic Ligands: An Octanuclear

(56) References Cited

OTHER PUBLICATIONS

Au4Cu4 Cluster and Luminscence Polymorphism in Au3Cu2 Clusters," J. Am. Chem. Soc. 132:12307-12318, 2010.

Mansour et al., "Linear Chain Au(I) Dimer Compounds as Environmental Sensors: A Luminescent Switch for the Detection of Volatile Organic Compounds," J. Am. Chem. Soc. 120:1329-1330.

McGee et al., "Inefficient Crystal Packing in Chiral [Ru(phen)3](PF6)2 Enables Oxygen Molecule Quenching of the Solid-State MLCT Emission," J. Am. Chem. Soc. 131:1896-1902, 2009.

Muro et al., "Microarray pattern recognition based on PtII terpyridyl chloride complexes: vapochromic and vapoluminescent response," Chem. Commun. pp. 6134-6136, 2008.

Nakajima et al., "Interconversion between Polymeric Orange and Monomeric Green Forms of a Schiff Base-Oxovanadium(IV) Complex," Bull. Chem. Soc. Jpn. 69:3207-3216, 1996.

Ni et al., "Luminescence vapochromic properties of a platinum(II) complex with 5,5'-bis (trimethylisilylethynyl)-2,2'-bipyridine," Chem. Commun. pp. 3801-3803, 2009.

Ni et al., "Luminescence Vapochromism of a Platinum(II) Complex for Detection of Low Molecular Weight Halohydrocarbon," Inorg. Chem. 48:10202-10210, 2009.

Pattacini et al., "Phosphino-Aminothiazoline Platinum(II) and Platinum(II)/Gold(I) Complexes: Structural, Chemical and Vapoluminescent Properties," Chem. Eur. J. 13:10117-10128, 2007.

Schwerdtfeger et al., "Stability of the Gold(I)-Phosphine Bond. A Comparison with Other Group 11 Elements," Inorg. Chem. 42:1334-1342, 2003.

Supriya et al., "Reversible Single Crystal to Single Crystal Transformation through Fe—O(H)Me/Fe—OH2 Bond Formation/Bond Breaking in a Gas-Solid Reaction at an Ambient Condition," J. Am. Chem. Soc. 129:3464-3465, 2007.

Terrones et al., "Volatile-organic-compound optic fiber sensor using a gold—silver vapochromic complex," Optical Engineering. 45(4):044011-044017, 2006.

Wadas et al., "Vapochromism and Its Structural Basis in a Luminescent Pt(II) Terpyridine-Nicotinamide Complex," J. Am. Chem. Soc. 126:16841-16849, 2004.

Yip et al., "Synthesis, structure and luminescence studies of heterometallic gold(I)—copper(I) and -silver(I) alkynyl clusters/aggregates," Photochem. Photobiol. Sci. 6:365-371, 2007.

Zeng et al, "Apical Ligand Substitution, Shape Recognition, Vapor-Adsorption Phenomenom, and Microcalorimetry for a Pillared Bilayer Porous Framework That Shrinks or Expands in Crystal-to-Crystal Manners upon Change in the Cobalt(II) Coordination Environment," Inorg. Chem. 48:7070-7079, 2009.

Abstract: "Vapochromism, Luminescence, Birefringence and Magnetism of d10-Metal Cyanide-based Coordination Polymers," Daniel B. Leznoff et al., The 61st American Chemical Society Northwest Regional Meeting, Jun. 25-28, 2006.

VAPOCHROMIC MATERIALS AND METHODS OF MAKING AND USING SAME

CROSS-REFERENCE TO RELATED APPLICATIONS

This application claims the benefit of U.S. Provisional Application No. 61/502,569, filed Jun. 29, 2011, which is hereby incorporated by reference herein in its entirety.

GOVERNMENT LICENSE RIGHTS

This invention was made with government support under contract CHE-0549902 awarded by the National Science Foundation. The government has certain rights in the invention.

TECHNICAL FIELD

The present invention relates generally to gold-copper complexes, and, more specifically to vapochromic gold-copper complexes, which respond to organic compounds and exhibit reversible luminescence color changes, and methods of making and using same.

BACKGROUND

Vapochromic materials suitable for sensing volatile organic compounds (VOCs) by the alteration of auro- and metallophilic attractions have attracted considerable attention. Whereas these systems often include metallophilic Pt—Pt, Au—Tl, Au—Au, and Au—Ag interactions, complexes with Au—Cu metal centers are generally less common, and such vapochromic complexes are understood to have not been reported.

The mechanism associated with the vapochromic response typically involves reversible rearrangements catalyzed by solvent vapor or interstitial solvation of transition metal complexes. Additionally, solid-vapor reactions involving the exchange of ligands coordinated to metal centers are quite rare. However, solvents are known to reversibly replace $H_2O$ at Fe centers and Co centers of certain solid state metal complexes, and $HCl_{(g)}$ has been observed to add reversibly to $[CuCl_2L_2]$ (L=3-chloropyridine, 3-bromopyridine) and thereby afford $[HL]_2(CuCl_4)$. Further, the viability of ligand exchange in metal complex polymers of the general formula $[CuL_n](Au(CN)_2)_2$ utilizing solvent vapors with different functional groups has been disclosed in U.S. Patent Application Publication No. 2009/0130768.

Vapochromic materials have recently been incorporated in chemical sensor devices. For example, $[Au—(PPh_2C(CSSAuC_6F_5)PPh_2Me)_2][ClO_4]$ has been used in the development of an optical fiber VOC sensor. A vapochromic light emitting diode and a vapochromic photodiode have also been built using tetrakis(p-dodecylphenylisocyano) platinum tetranitroplatinate and bis(cyanide)-bis(p-dodecylphenylisocyanide)platinum(II), respectively.

Despite the foregoing, a need exists for new vapochromic materials that may be suitable for use in chemical sensor devices, such as VOC sensors.

SUMMARY OF THE INVENTION

Certain aspects of the present disclosure are described in the appended claims. There are additional features and advantages of the subject matter described herein. They will become apparent as this specification proceeds. In this regard, it is to be understood that the claims serve as a brief summary of varying aspects of the subject matter described herein. The various features described in the claims and below for various embodiments may be used in combination or separately. Any particular embodiment need not provide all features noted above, nor solve all problems or address all issues noted above.

According to an embodiment of the invention, a vapochromic gold-copper complex of a general formula $[Au(L)_2(Cu(Y)_n)_2]^{+3}X_3$ is provided, in which L is an N-heterocyclic carbene (NHC); Y is a heteroatom-containing ligand; X is an anion, and n is an integer having a value of 1 or 2, and solvates thereof.

According to another embodiment of the invention, a chemical sensor device is provided, wherein the device includes the vapochromic gold-copper complex of the general formula $[Au(L)_2(Cu(Y)_n)_2]^{+3}X_3$, wherein L, Y, X, and n are the same as defined above.

According to yet another embodiment, a method of detecting an analyte includes (a) exposing a first complex to the analyte, wherein the first complex is a vapochromic gold-copper complex having the general formula of: $[Au(L)_2(Cu(Y)_n)_2]^{+3}X_3$, wherein L, Y, X, and n are the same as defined above, and wherein the first complex is reversibly transformed to a second complex by replacement of at least one of the heteroatom-containing ligands by the analyte upon exposing the first complex to the analyte; and (b) observing a photoluminescent or infrared absorbance change in the second complex relative to the first complex resulting from exposure to the analyte.

According to yet another embodiment, a method of making a vapochromic gold-copper complex of a general formula $[Au(L)_2(Cu(Y)_n)_2]^{+3}X_3$, where L, Y, X, and n are the same as defined above, is provided, The method includes reacting the N-heterocyclic carbene with a silver compound to form a bis-N-heterocyclic carbene silver complex in a first solvent; forming a bis-N-heterocyclic carbene gold complex by reacting the bis-N-heterocyclic carbene silver complex with a gold compound in a second solvent; and forming the vapochromic gold-copper complex by reacting the bis-N-heterocyclic carbene gold complex with a copper compound in a third solvent, wherein the first, second, and third solvents may be the same or different.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF EMBODIMENTS

Figure 1:
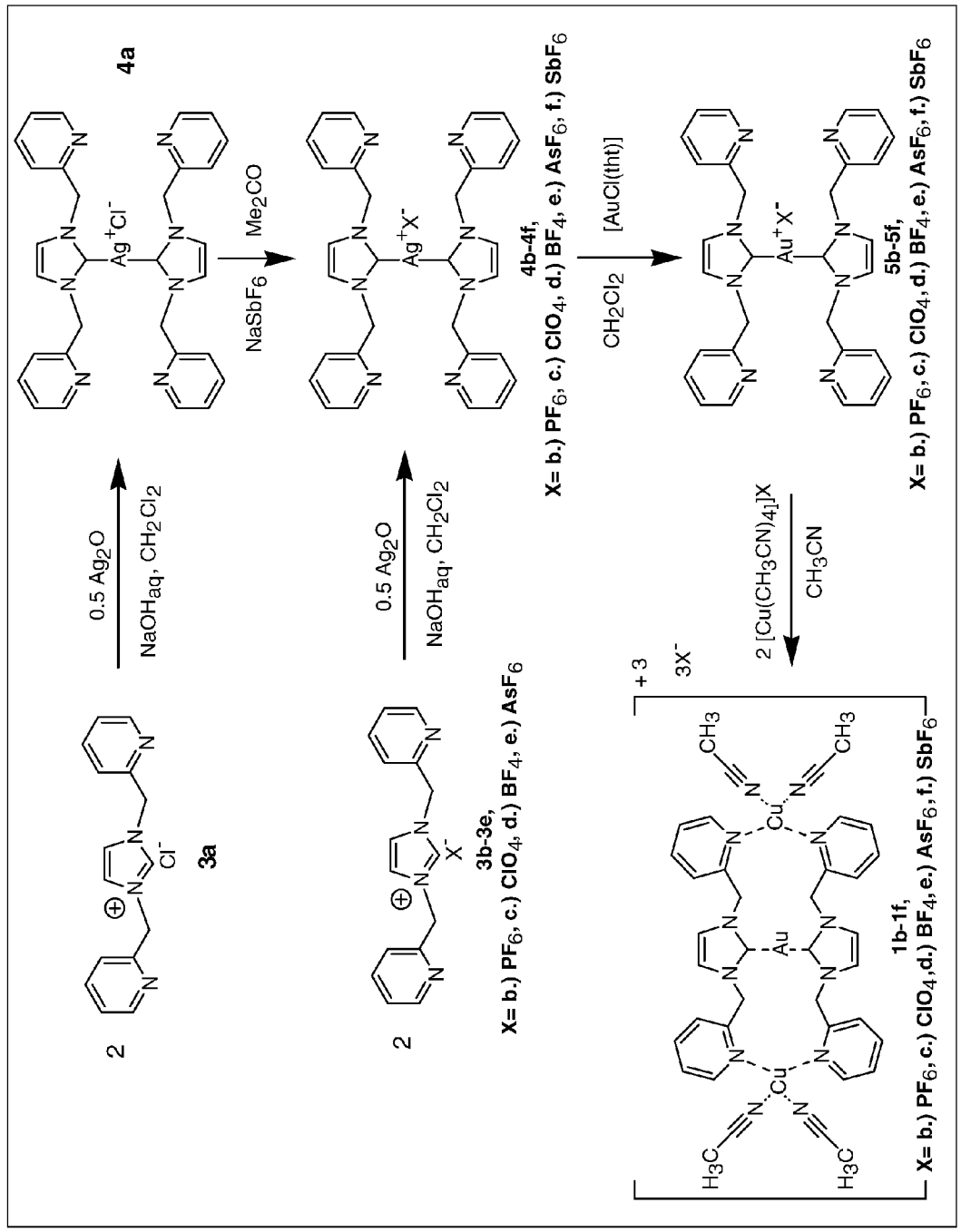
FIG. 1 is a depiction of exemplary synthetic routes for the preparation of vapochromic Au—Cu complexes, in accordance with an embodiment of the present invention.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, as well as A and B together.

As used herein, a "compound" can be a molecular compound held together by covalent bonds, a salt held together by ionic bonds, an intermetallic compound held together by metallic bonds, or a complex held together by coordinate covalent bonds.

The present invention is directed to vapochromic materials, particularly N-heterocyclic Au(I) carbene complexes that modulate their vapochromic response through changes in ligation and subsequent formation or cleavage of short Au—Cu interactions depending on the ligand(s). Moreover, methods of making the vapochromic materials and using the same, such as in chemical sensor devices, as well as methods of detecting an analyte, such as a volatile organic compound (VOC), are provided.

According to one embodiment of the invention, a vapochromic gold-copper complex is provided having the general formula of: [Au(L)$_2$(Cu(Y)$_n$)$_2$]$^{+3}$X$_3$, where L is an N-hetero-cyclic carbene; Y is a heteroatom-containing ligand; X is an anion, and n is an integer having a value of 1 or 2, and solvates thereof.

In one example, the N-heterocyclic carbene (NHC) is of the general formula:

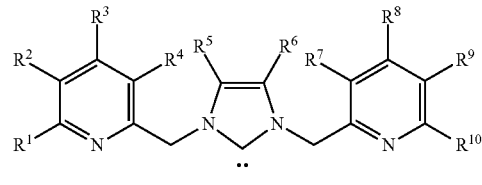

wherein R$^1$ through R$^{10}$ are substituents that do not diminish the photoluminescent and/or infrared absorbance properties of the complex to a non-useful amount. For example, R$^1$ through R$^{10}$ can be independently selected from hydrogen, an alkyl, aryl, alkaryl, alkenyl, cycloalkyl, heteroalkyl, heteroaryl, or a halide. In one example, R$^1$ through R$^{10}$ are each hydrogen.

According to embodiments of the invention, the heteroatom-containing ligand includes a hetero (non-carbon) atom donor, such as oxygen, nitrogen, phosphorus, or sulfur, which optionally may be incorporated into a heterocyclic ring. Accordingly, Y may be water, an alcohol, a nitrile, a ketone, an aldehyde, a carboxylic ester, a carbonic ester, an amine, an imine, a thioether, a phosphonic ester, a phosphoric ester, or a phosphorous ester. For example, Y may be water. In other embodiments, L may be an organic compound selected from the group consisting of methanol, ethanol, acetone, methyl ethyl ketone, tetrahydrothiophene, dimethylsulfide, acetonitrile, and a phosphorus-containing compound.

In another example, the anion moiety of the vapochromic gold-copper complex is a weakly or non-coordinating anion. In one example, the non-coordinating anion can be selected from PF$_6^-$, BF$_4^-$, AsF$_6^-$, SbF$_6^-$, or ClO$_4^-$.

According to another embodiment, the vapochromic gold-copper complex can have the formula:

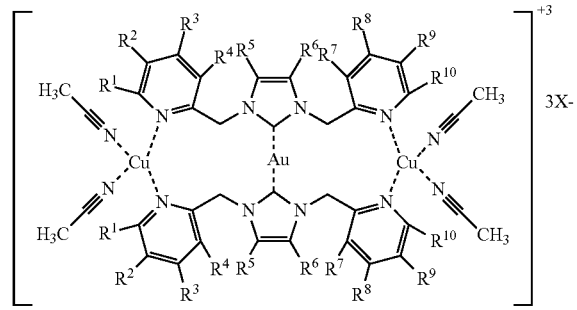

wherein R$^1$ through R$^{10}$ are independently selected from hydrogen, an alkyl, aryl, alkaryl, alkenyl, cycloalkyl, heteroalkyl, heteroaryl, or a halide; and wherein X is a non-coordinating monovalent anion. In one example, R$^1$ through R$^{10}$ are each hydrogen (as shown in Scheme 1 below), which possesses a reversible identity and corresponding luminescence color changes, as discussed below.

SCHEME 1: Reversibility of Complexes 1 and 2.

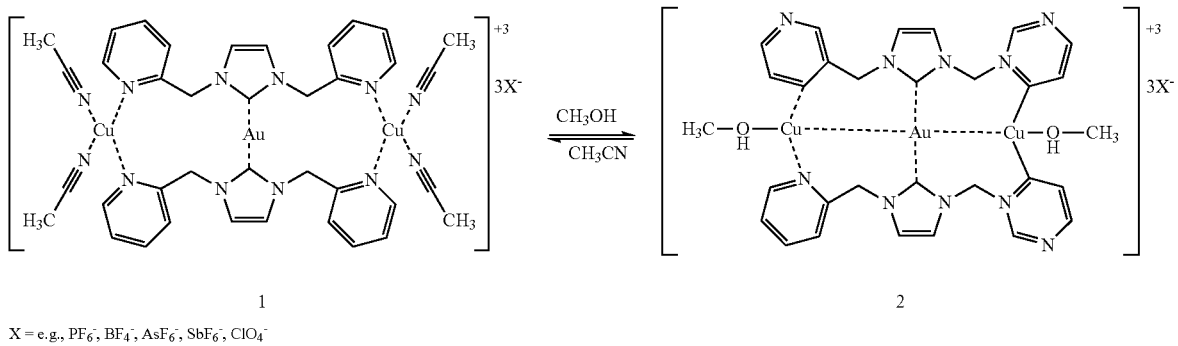

X = e.g., $PF_6^-$, $BF_4^-$, $AsF_6^-$, $SbF_6^-$, $ClO_4^-$

According to an embodiment of the present invention, a method of making a vapochromic gold-copper complex of a general formula $[Au(L)_2(Cu(Y)_n)_2]^{+3}X_3$, where L, Y, X, and n are the same as defined above, is provided. The method includes reacting the N-heterocyclic carbene with a silver compound to form a bis-N-heterocyclic carbene silver complex in a first solvent; forming a bis-N-heterocyclic carbene gold complex by reacting the bis-N-heterocyclic carbene silver complex with a gold compound in a second solvent; and forming the vapochromic gold-copper complex by reacting the bis-N-heterocyclic carbene gold complex with a copper compound in a third solvent, wherein the first, second, and third solvents may be the same or different. Examples of suitable solvents include, but are not limited to, alcohols, esters, ethers, halogenated hydrocarbons, ketones, and nitriles. For example, according to an embodiment, solvents such as dichloromethane, acetone, and acetonitrile may be used for making the vapochromic gold-copper complex.

For example, as shown in FIG. 1, complementary synthetic approaches to synthesizing vapochromic gold-copper complexes, such as generic complex 1 above, include treating 1,3-bis[(2-pyridyl)methyl]-2H-imidazolium chloride (3a) with half a stoichiometric equivalent of silver (I) oxide in the presence of aqueous sodium hydroxide and methylene chloride to form $[Ag(im(CH_2py)_2)_2]Cl$ (4a), which in turn can be subjected to an anion exchange reaction to provide complexes 4b-4f, where X=b.) $PF_6$, c.) $ClO_4$, d.) $BF_4$, e.) $AsF_6$, f.) $SbF_6$. It should be noted that the appropriate 1,3-bis[(2-pyridyl) methyl]-2H-imidazolium salt (3b-3e) can be taken directly to its corresponding bis[1,3-bis((2-pyridyl)methyl)imidazol-2-ylidene]silver(I) complex (4b-4-e) with the exception of the $SbF_6^-$ salt on account of the base sensitivity of the hexafluoroantimonate anion. The silver(I) complexes can also be represented by the formula designation $[Ag(im(CH_2py)_2)_2]X$, where $im(CH_2py)_2)_2$ represents 1,3-bis[(2-pyridyl)methyl]-2H-imidazol-2-ylidene carbene ligand and X is b.) $PF_6$, c.) $ClO_4$, d.) $BF_4$, e.) $AsF_6$, f.) $SbF_6$.

Treatment of the silver(I) complex 4b-4-f with an appropriate gold(I) reagent, e.g., AuCl(tht), where tht=tetrahydrothiophene, or $AuCl(S(CH_3)_2)$, provides [Au $(im(CH_2py)_2)_2]X$ 5b-5f, which when combined with two equivalents of copper (I) acetonitrile complex provides the vapochromic gold-copper complexes 1b-1f, each of which are generally depicted as complex 1 in Scheme 1 above.

In a direct complementary approach, the gold compounds having a general formula $[Au(im(CH_2py)_2)_2]X$ could also be prepared by direct methods from a gold starting material [AuCl(SR_2)], (SR_2=any cyclic or acyclic alkyl thioether or aralkyl thioether), [AuCl(CO)], [AuCl(PR_3)] (PR_3=any tertiary phosphine ligand), Q[AuX_4] (Q=any compatible cation, X=halide or pseudo-halide), the ligand precursor H[im (CH_2py)_2] and a suitable base as is described in literature. Examples of suitable bases include alkaline metal bases such as sodium hydroxide. In one example, the colorless [Au(im $(CH_2py)_2)_2(Cu(MeCN)_2)_2](PF_6)_3$ (1b) is formed by the simple addition of two equivalents of $[Cu(MeCN)_4]PF_6$ to $[Au(im(CH_2py)_2)_2]PF_6$ (5b) in acetonitrile.

As generally depicted in Scheme 1, when X is $PF_6$, solid samples of complex 1b, or complex 1b.2MeCN, can react with MeOH vapor and thereby cause a physical change to the complex, which in turn affects the photoluminescent properties of the complex. For example, upon reaction of complex 1b with MeOH, a green luminescent ($\lambda_{max}$=520 nm) species is produced, which is understood to be of the chemical structure $[Au(im(CH_2py)_2)_2(Cu(MeOH))_2](PF_6)_3$ (2b), and which is generally depicted in Scheme 1 as complex 2. Alternatively, complex 1b is sparingly soluble in liquid MeOH but reacts to form complex 2b. This process can be facilitated by gentle heating. Crystallization from MeOH/Et_2O mixtures produces a bluish-green luminescent species of complex 2b.2MeOH.2Et_2O.

Figure 3:
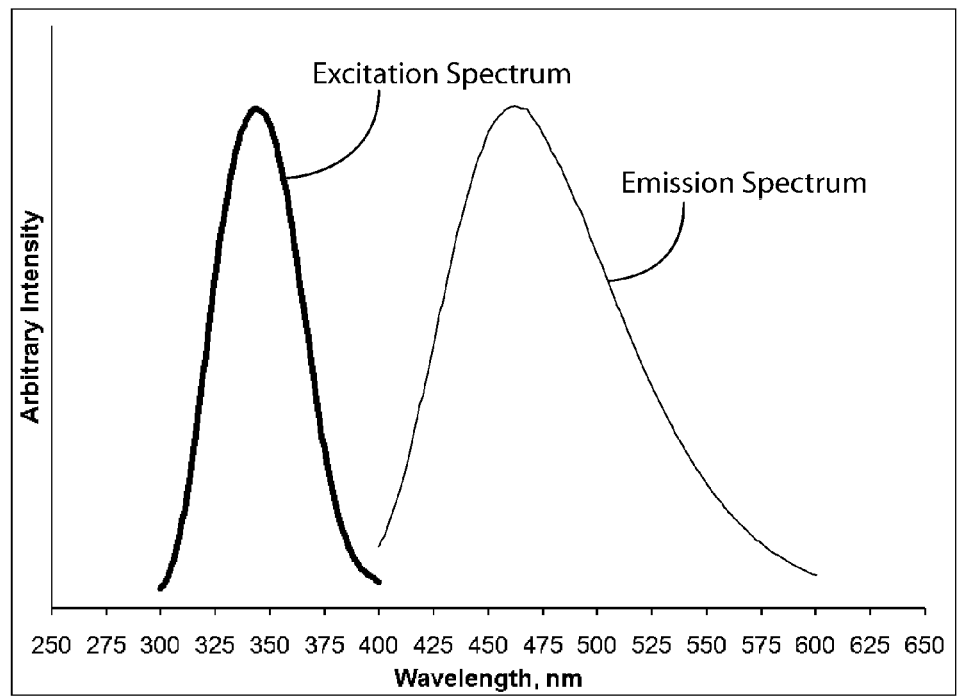
FIG. 3 is a spectrum showing the excitation and emission bands of complex 1b.
Figure 4:
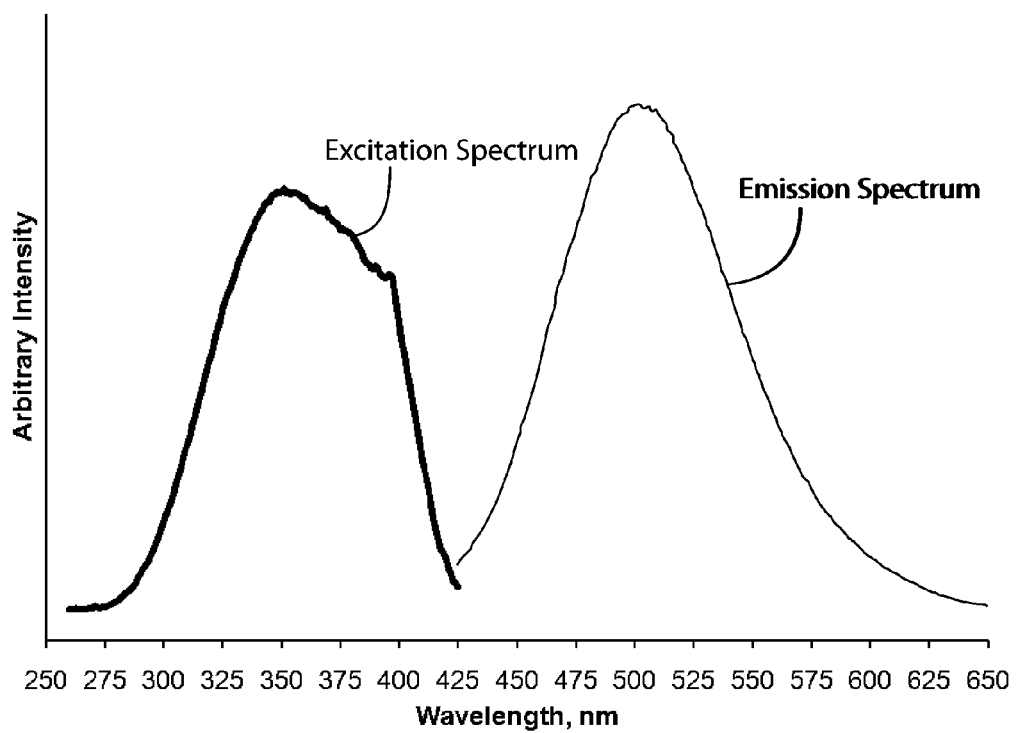
FIG. 4 is a spectrum showing the excitation and emission bands of crystalline complex 2b.2MeOH.2Et$_2$O.
Figure 5:
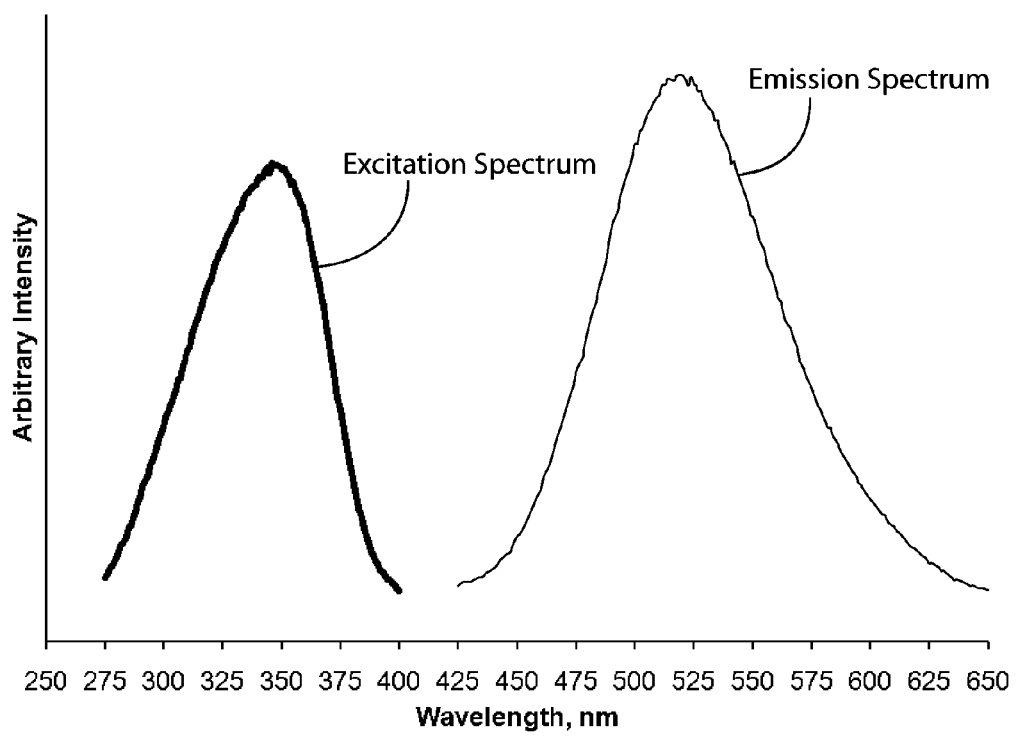
FIG. 5 is a spectrum showing the excitation and emission bands of complex 1b treated with dry MeOH vapor.
Figure 6:
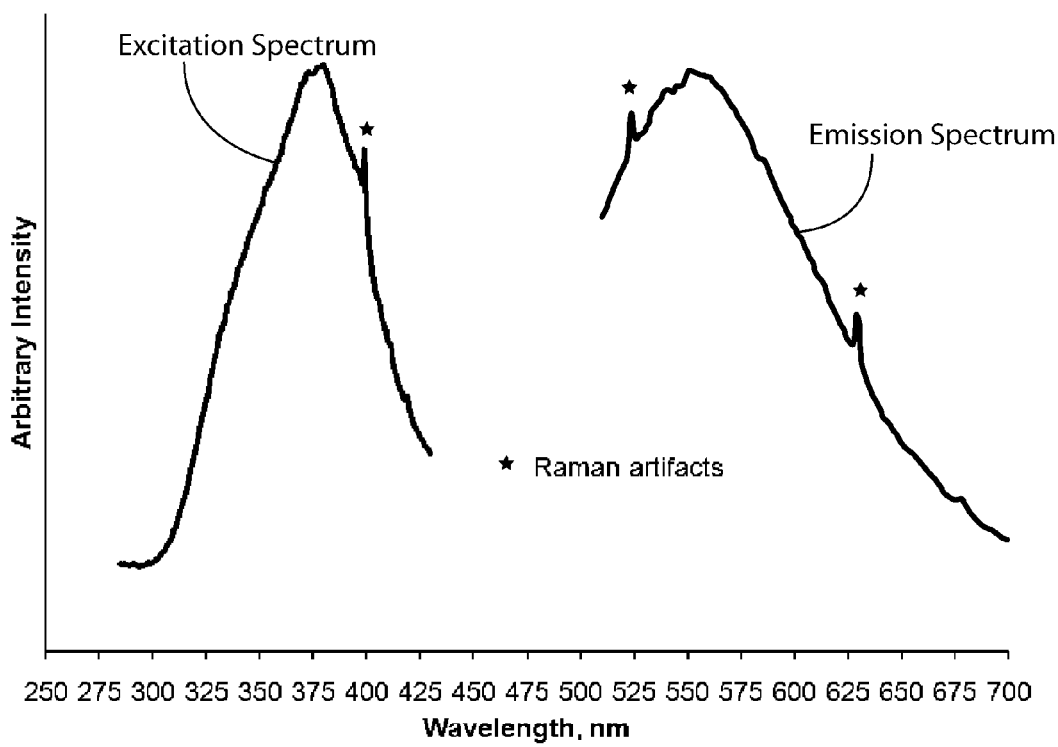
FIG. 6 is a spectrum showing the excitation and emission of complex 1b treated with dry MeOH vapor then exposed to the atmosphere.
Figure 7:
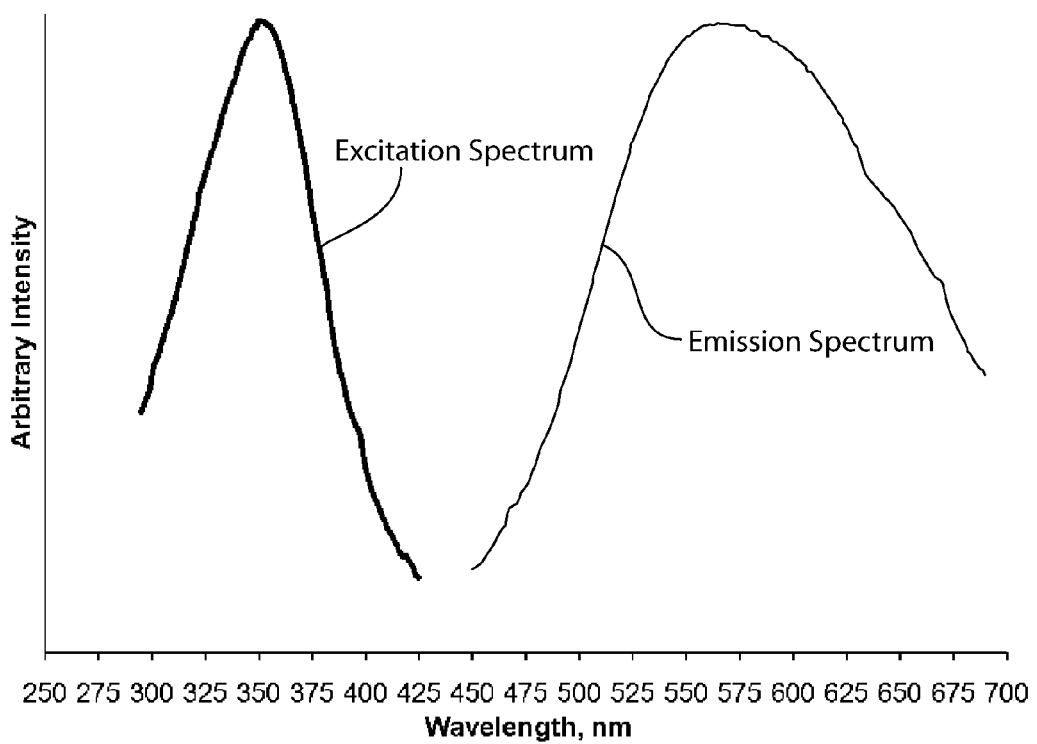
FIG. 7 is a spectrum showing the excitation and emission bands of complex 1b treated with dry MeOH vapor and evacuated.
Figure 8:
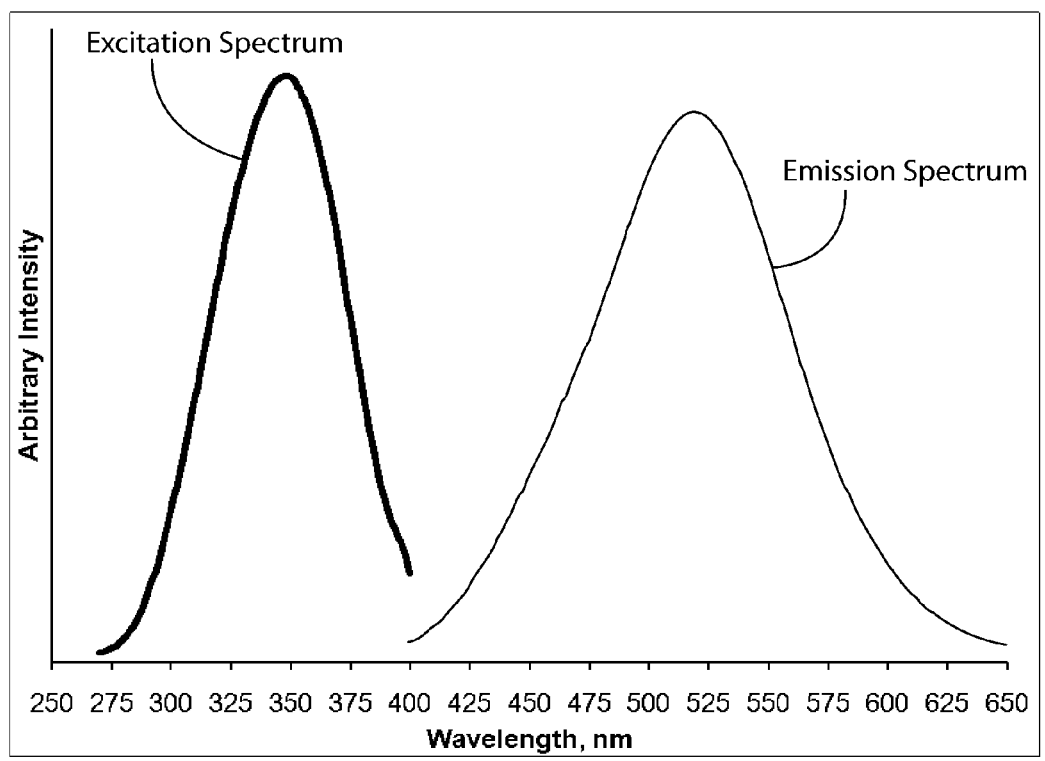
FIG. 8 is a spectrum showing the excitation and emission bands of complex 1b treated with H$_2$O vapor.

Crystal structures of complex 1b.2MeCN and complex 2b.2MeOH.2Et_2O were obtained from using single crystal X-ray analysis and the x-ray crystallographic data of each are provided in Table 1 below. Referencing the molecular structure of crystallized complex 1b.2MeCN, the complex exhibits a proper mirror plane normal to the Au(NHC)_2 plane, and the cation furthermore shows $C_2$ pseudo-symmetry along the axis formed by the metal atoms. However, this overall $C_2$ pseudo-symmetry is not crystallographically-supported due to an asymmetric arrangement of free (non-coordinated) MeCN molecules above and below the Au(NHC)_2 plane. The X-ray crystal structure of complex 1b.2MeCN also reveals a nearly linear $Au^I$ center coordinated to two NHC ligands whose picolyl arms bridge two $[Cu(MeCN)_2]^+$ moieties with long and presumably repulsive Au(I)—Cu(I) separations of ~4.6 Å. Channels occupied by MeCN molecules are running along the a axis, which may be responsible for efficient exchange of solvent molecules upon vapor treatment. Additionally, the acetonitrile molecules are positioned collinear to the C—Au—C vector approximately 3.8 to 5.4 Å from the $Au^I$ center. These two lattice MeCN molecules are lost upon evacuation of the crystals or prolonged exposure to air affording the blue-emitting 1b ($\lambda_{max}$ 462 nm, FIG. 3).

Referencing the molecular structure of crystallized complex 2b.2MeOH.2Et$_2$O, each MeOH at the copper centers forms a hydrogen bond chain via a lattice MeOH terminating in a lattice Et$_2$O. The picolyl arms of the ligands adopt an up/down (UD) geometry relative to the Au(NHC)$_2$ plane instead of the UU and DD arrangements found in the crystals of complex 1b.2MeCN, because of this motif a C$_2$ axis through the C—Au—C atoms is found in place of the mirror plane. The Cu(I)—Au(I)—Cu(I) angle measure 153.02(3)°. Again channels are found running parallel to the a axis which contain MeOH, Et$_2$O and PF$_6^-$ moieties.

In further reference to crystallized 2b.2MeOH.2Et$_2$O, two MeCN ligands on each Cu(I) center of complex 1b are replaced by a single MeOH molecule in complex 2b. This simple ligand substitution reaction induces a non-trivial metal reorganization. In the absence of a second coordinating solvent, each Cu(I) center completes its tetrahedral coordination geometry through ligation to the Au(I) center with short (and attractive) Au—Cu contacts of 2.7915(7) Å. Unlike complex 1b.2MeCN, the lattice solvates of complex 2b.2MeOH.2Et$_2$O reside away from the metal centers. Also noteworthy, the picolyl arms on each NHC ligand in complex 2b twist to alternate faces of the complex.

Figure 13:
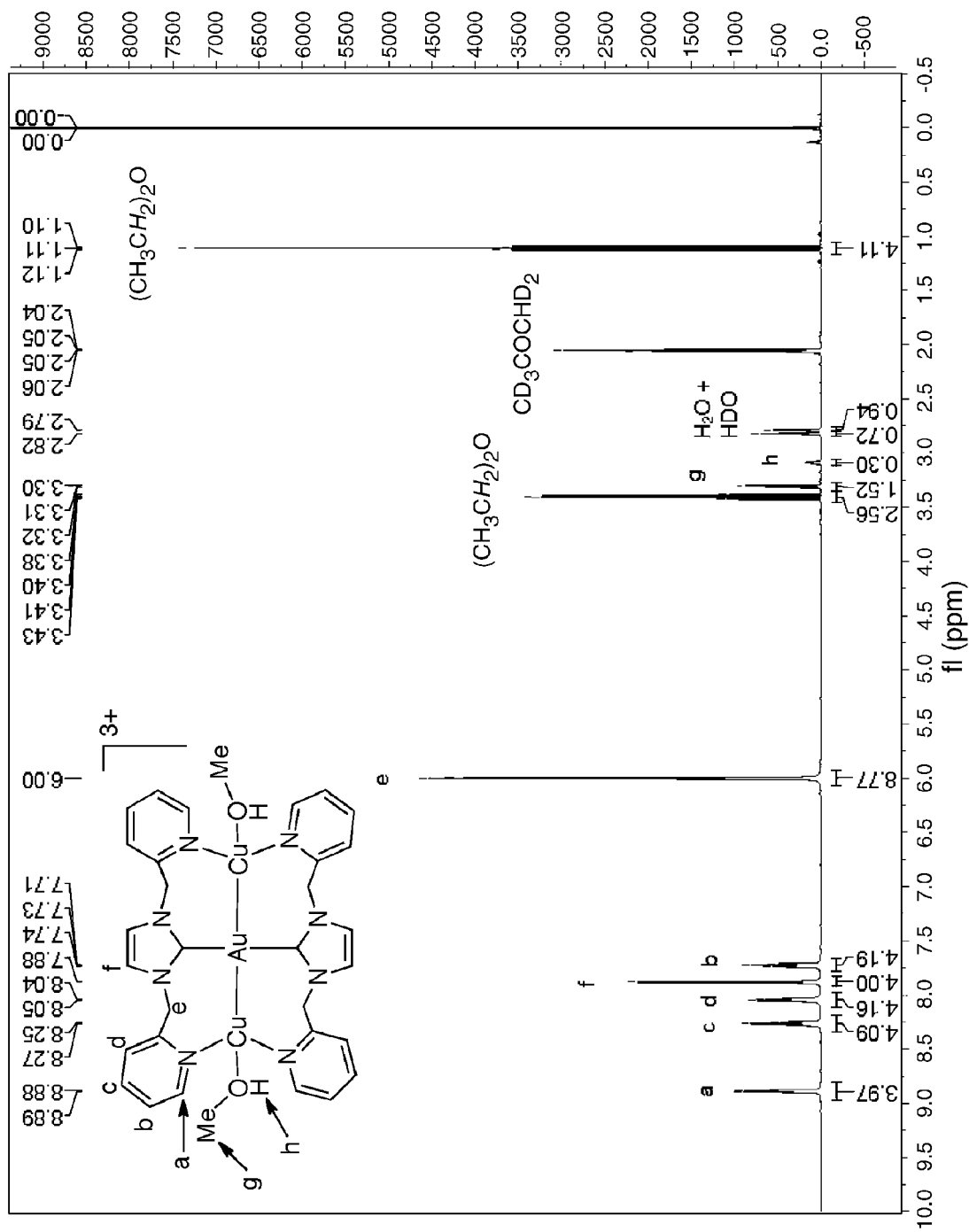
FIG. 13 is a $^1$H NMR spectrum of complex 2b exposed to vacuum.
Figure 14:
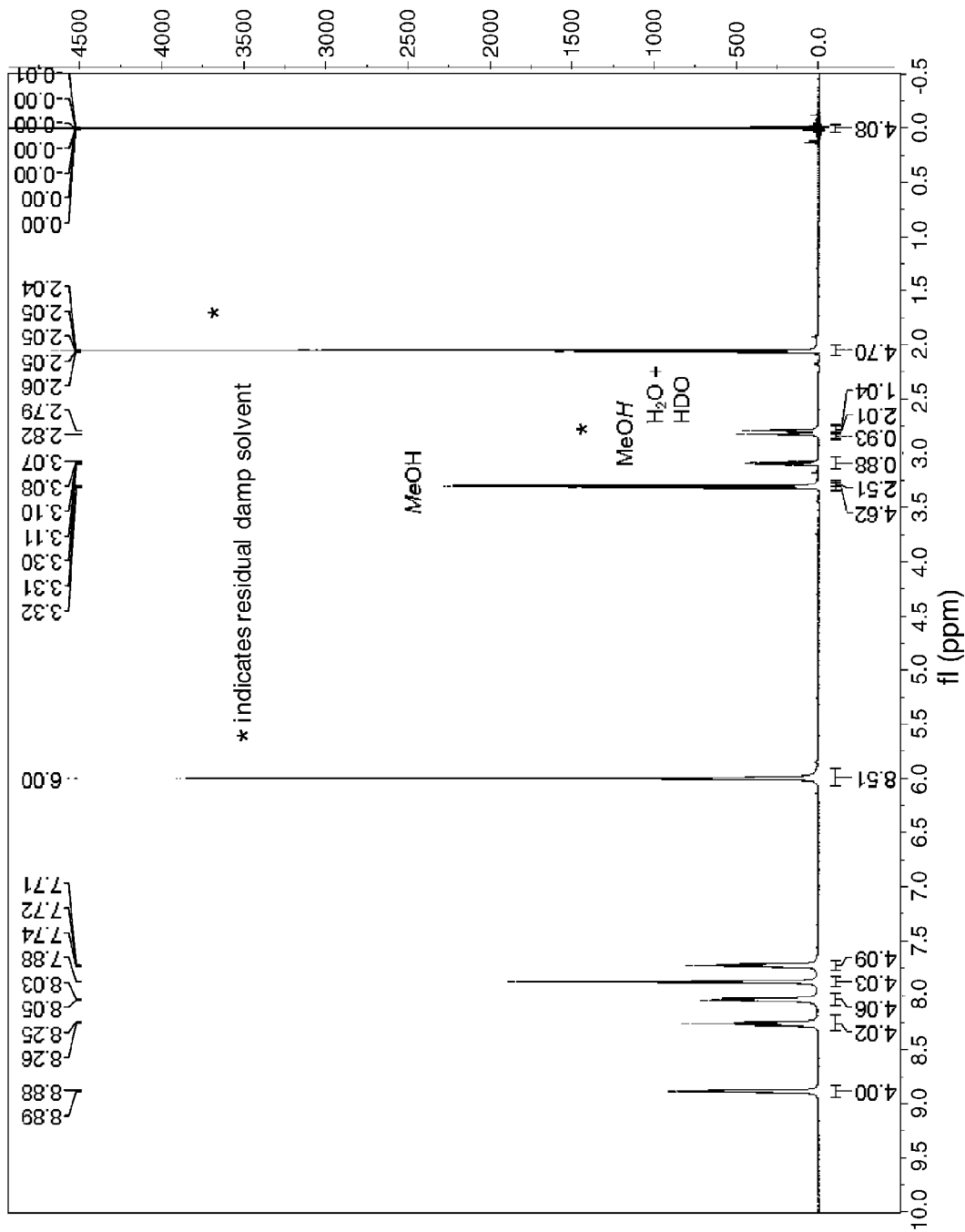
FIG. 14 is a $^1$H NMR spectrum of complex 1b treated with dry MeOH.

While the methanol content of the crystals of complex 2b.2MeOH.2Et$_2$O can be reduced upon evacuation, the diethyl ether is not substantially changed, thereby leaving a diethyl ether hemisolvate, as evidenced by NMR spectroscopy (FIG. 13) and elemental analysis. While not being bound by any particular theory, this seemingly counterintuitive behavior could be the result of Et$_2$O being unable to evacuate the crystal due to steric constraints, which are not experienced by the smaller MeOH molecules. Similar results of crystal structures changing upon evacuation of solvent and blocking its complete removal have been reported.

Vapochromic materials, such as the gold-copper complexes described herein, display photoluminescent or infrared absorption changes upon exposure to certain vapors of analytes, such as water, an organic molecule selected from an alcohol, a nitrile, a ketone, an aldehyde, a carboxylic ester, a carbonic ester, an amine, an imine, a thioether, a phosphonic ester, a phosphoric ester, or a phosphorous ester, or combinations thereof. As such, these photoluminescent or infrared absorption changes may be utilized to obtain a sensor response. For example, upon excitation with UV light (e.g., $\lambda$=300 to 400 nm) at room temperature, the vapochromic gold-copper complexes described herein are emissive. Therefore, in accordance with another embodiment of the invention, a chemical sensor device is provided, wherein the device includes the vapochromic gold-copper complex of the general formula [Au(L)$_2$(Cu(Y)$_n$)$_2$]$^{+3}$X$_3$, wherein L, Y, X, and n are the same as defined above.

Accordingly, in yet another embodiment of the present invention, a method of detecting an analyte is provided. The method includes exposing a first complex to the analyte, wherein the first complex is a vapochromic gold-copper complex having the general formula of: [Au(L)$_2$(Cu(Y)$_n$)$_2$]$^{+3}$X$_3$, wherein L, Y, X, and n are the same as defined above. During the exposing, the first complex is reversibly transformed to a second complex by replacement of at least one of the heteroatom-containing ligands by the analyte upon exposing the first complex to the analyte. The method further includes observing a photoluminescent or infrared absorbance change in the second complex relative to the first complex resulting from exposure to the analyte.

Shown in FIGS. 2-9 are emission (luminescence) and excitation (absorption) curves of the vapochromic gold-copper complexes 1b after exposure to different solvents and conditions. When complex 1b is treated with MeOH vapor generated without drying the solvent or the N$_2$ stream, the luminescence observations roughly follow the results obtained with dry MeOH vapor. However, analysis of the product obtained showed that H$_2$O is preferentially incorporated into the product according to $^1$H NMR (5.5 mole equivalents) revealing the presence of only a little MeOH (0.2 eq.). Also, the green luminescence does not immediately change to yellow upon exposure to the atmosphere. This delay is attributed to the water content. Upon evacuation of the powder obtained with commercial MeOH, a longer wavelength emission is found ($\lambda_{max}$ 603 nm). $^1$H NMR analysis of the evacuated powder reveals loss of some H$_2$O (residual amount 2.5 eq.) and MeOH (residual amount 0.1 eq.) content.

Likewise, complex 1b exposed to H$_2$O$_{(g)}$ shows green luminescence, which is stable under atmospheric conditions, and an emission change from green to orange is observed under vacuum with heating. However, the green to orange transition was not complete after 30 min. under the heated vacuum conditions.

The intensities of the luminescence spectra of complexes 1b and 2b are significantly different, and the emission of complex 1b treated with dry MeOH vapor as well as complex 2b.2MeOH.2Et$_2$O typically is about ten times lower than that of the original sample of complex 1b, after the former is exposed to the atmosphere the intensity decreases further; evacuation causes a higher luminescence intensity which is comparable to the one observed in original complex 1b.

Figure 11:
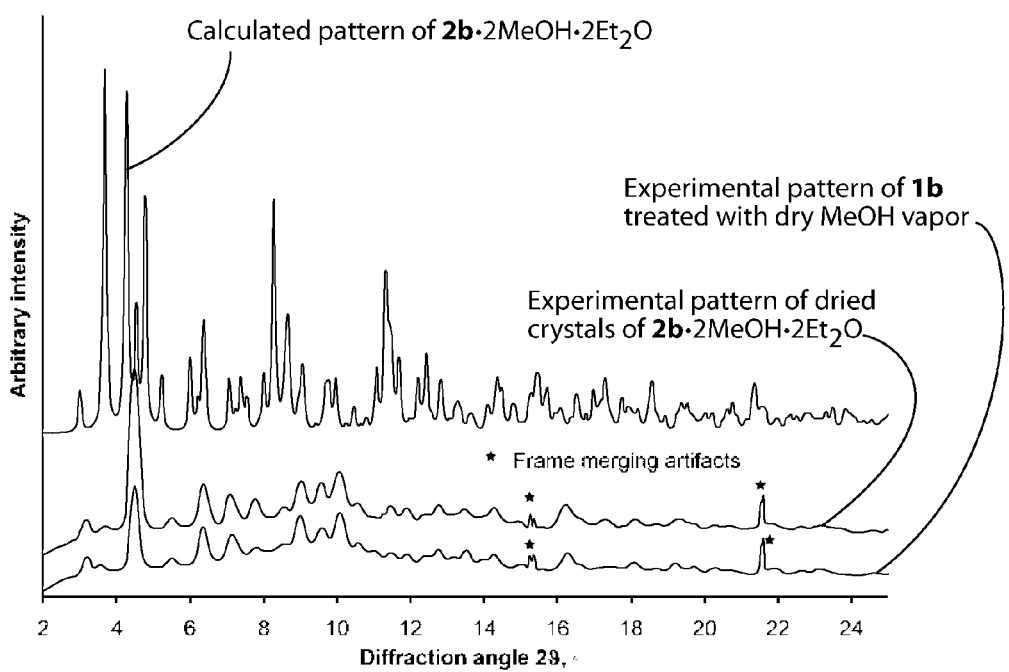
FIG. 11 is an X-ray powder diffraction patterns of complex 2b stacked for ease of comparison.
Figure 12:
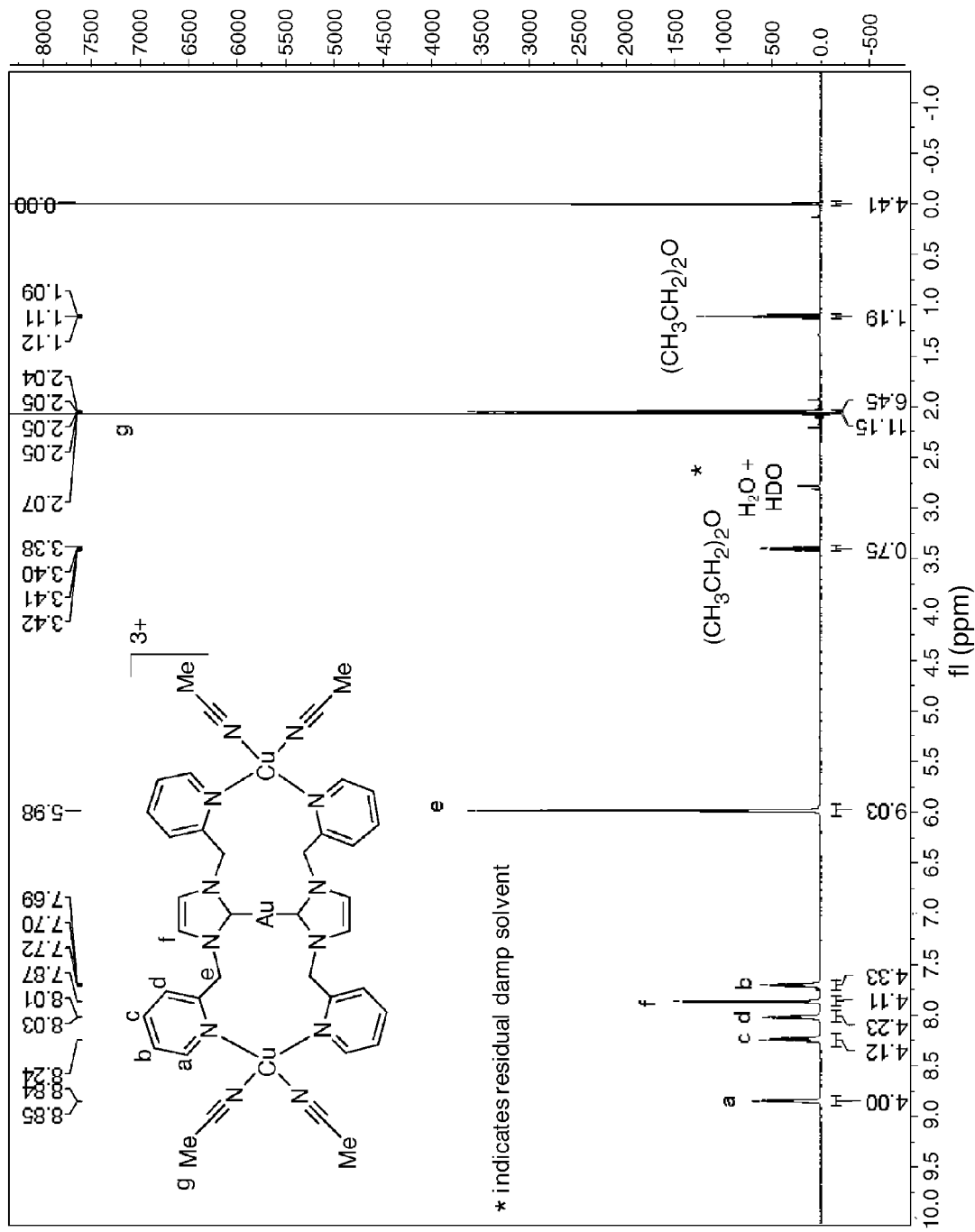
FIG. 12 is a $^1$H NMR spectrum of evacuated complex 1b showing four acetonitrile ligands.

Exposure to air or vacuum red-shifts the luminescence color of crystalline complex 2b.2MeOH.2Et$_2$O ($\lambda_{max}$ 502 nm) to 520 nm reinforcing the assigned composition depicted in Scheme 1. More conclusively, the X-ray powder pattern obtained from a vacuum dried sample of 2b.2MeOH.2Et$_2$O matches the pattern obtained by exposing 1b to dry MeOH vapor (FIG. 11). Both complexes 1b and 2b were additionally characterized by several additional methods and their spectroscopy and analyses are consistent with their proposed formulation.

Figure 2:
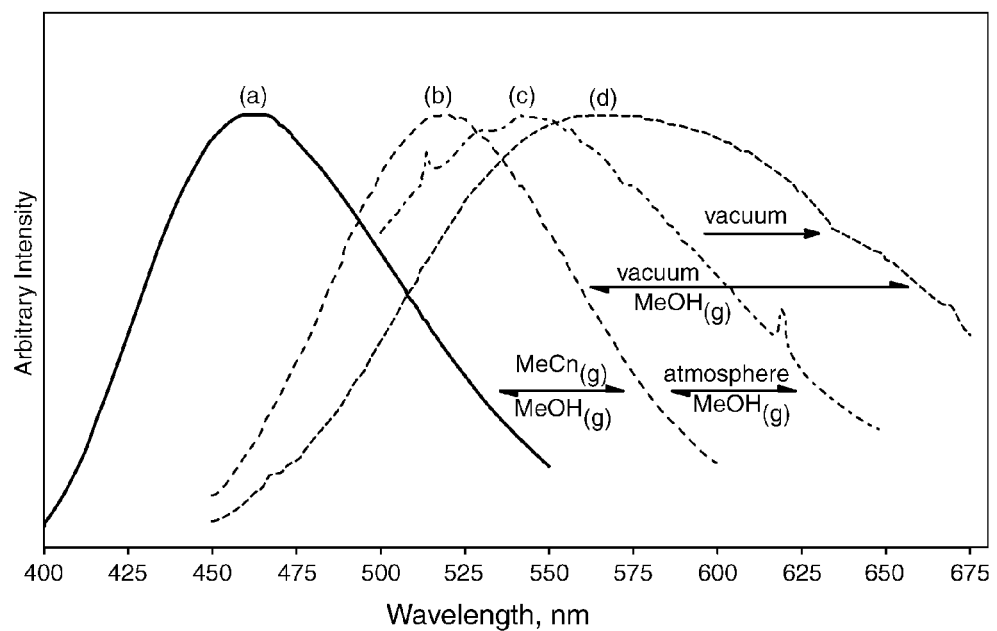
FIG. 2 is a normalized solid-state emission spectra ($\lambda_{exi}$=365 nm) showing transformations (a): complex 1b, (b): complex 2b formed by treating complex 1b with $MeOH_{(g)}$, (c): MeOH-treated complex 1b exposed to atmosphere, (d): MeOH-treated complex 1b exposed to vacuum, in accordance with embodiments of the present invention.
Figure 9:
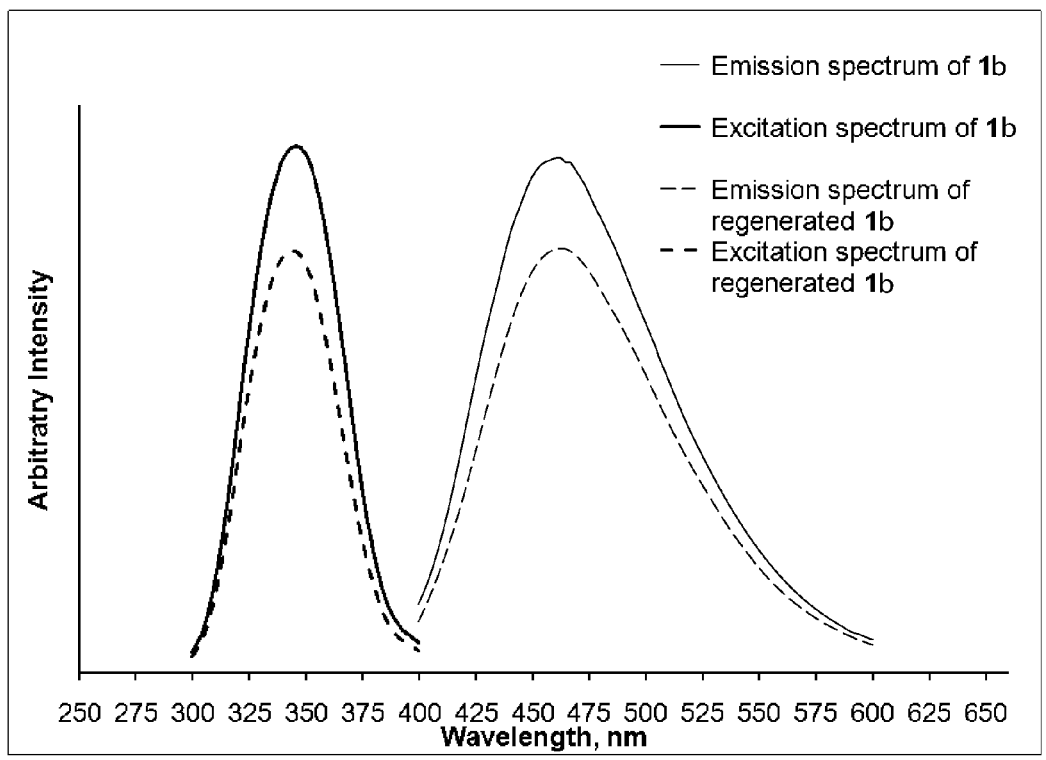
FIG. 9 is a spectrum showing the excitation and emission bands for complex 1b and complex 1b regenerated from complex 2b.
Figure 15:
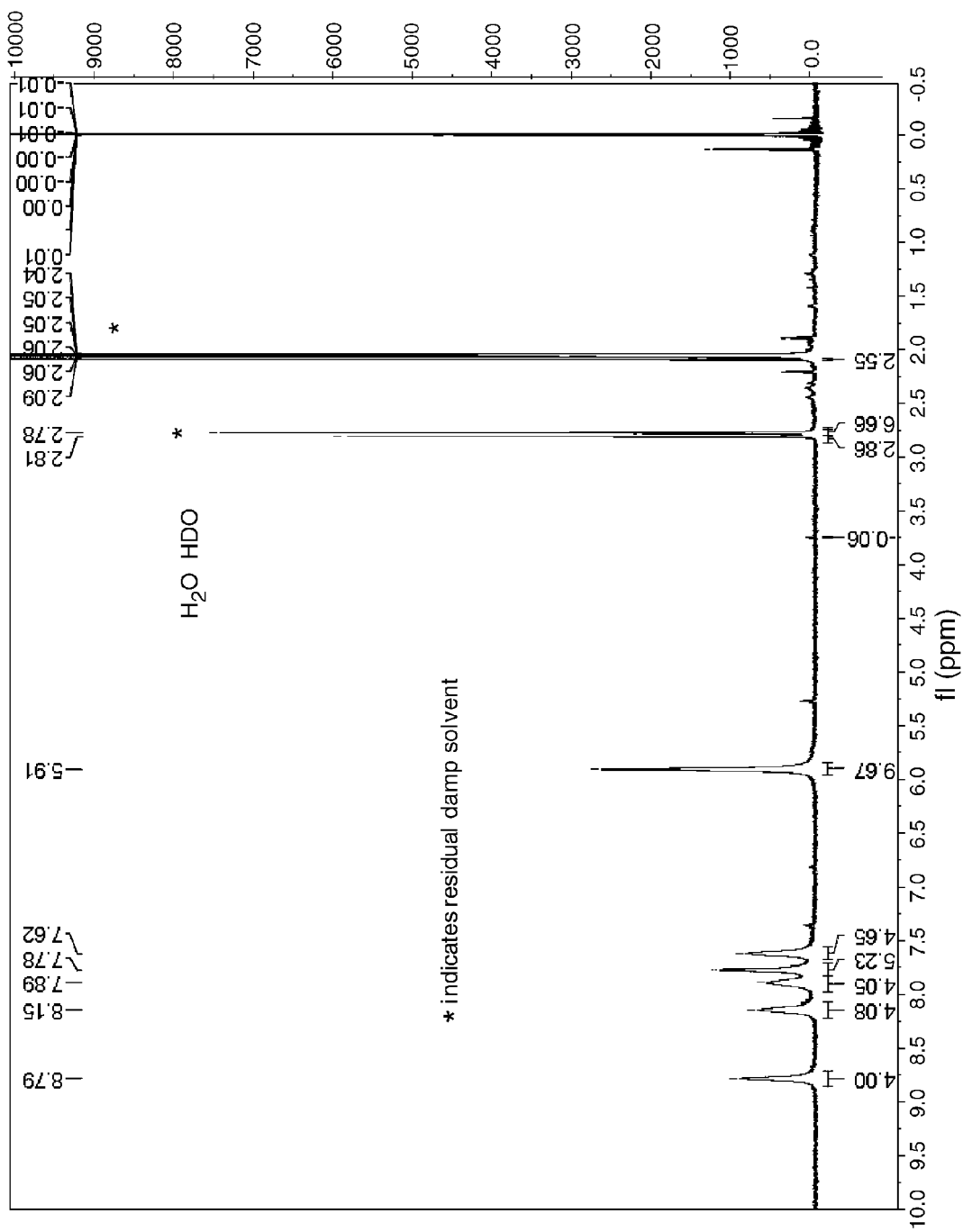
FIG. 15 is a $^1$H NMR spectrum of complex 1b treated with dry MeOH followed by evacuation showing no methanol or acetonitrile.
Figure 16:
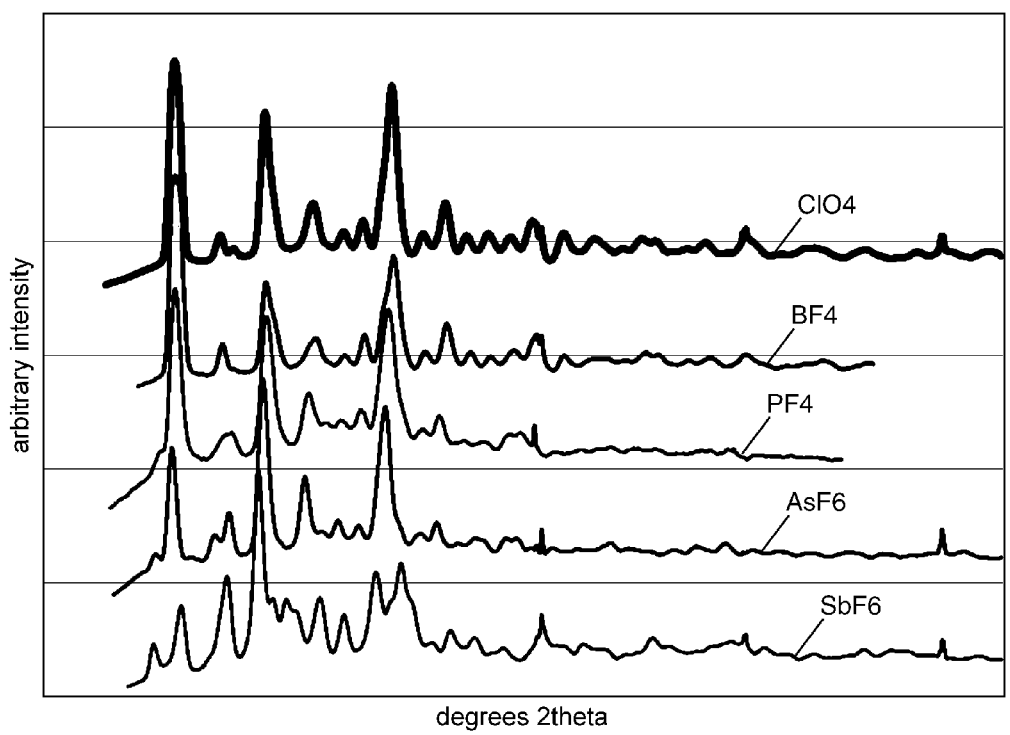
FIG. 16 is a powder X-ray diffractogram showing the patterns of various exemplary products (1b-1f), generated with Mo-Kα radiation (λ 0.71073 Å).

Complexes 1b and 2b (and their solvates) respond reversibly to organic molecule vapors, such as an alcohol, a ketone, a nitrile, an ester, or an ether, although complex 2b responds much more dramatically. Vapor experiments were conducted by passing a stream of a carrier gas, such as N$_2$, saturated with the respective organic molecule vapor onto powdered samples of complexes 1b or 2b. Methanol, H$_2$O or Me$_2$CO vapor effected changes in luminescence wavelength while CH$_2$Cl$_2$ and THF (tetrahydrofuran) vapors had no effect over the course of days. All of these species react with MeCN to regenerate complex 1b.2MeCN (FIG. 9). As shown in FIG. 2, when complex 1b.2MeCN is exposed to MeOH vapor the solid-state luminescence ($\lambda_{exi}$=365 nm) changes from (a) blue ($\lambda_{max}$ 462 nm) to (b) green ($\lambda_{max}$ 520 nm), and the emission intensity decreases. Notably, all of the MeCN molecules are completely exchanged, and no residual MeCN was detected in the material by either IR, $^1$H or $^{13}$C{$^1$H} NMR spectroscopy despite the nitrile's stronger affinity for Cu(I) compared to that of MeOH. Integration of the methanol signal suggests that one MeOH is added per copper center, along with some trace H$_2$O incorporation. Upon exposure to air, some of the MeOH is quickly lost producing a compound with faint (c) yellow emission ($\lambda_{max}$=543 nm). Re-exposure to dry MeOH vapor rapidly restores the (b) green luminescence. Exposing the MeOH containing species to vacuum produces a unique and fast luminescence change to (d) yellow-orange ($\lambda_{max}$=573 nm) which can be reversed by MeOH$_{(g)}$ to restore the (b) green ($\lambda_{max}$=520 nm) emitting species. $^1$H NMR analysis shows that this evacuated species is devoid of MeOH suggesting a coordinatively unsaturated Cu(I) center (see FIG. 15). Using vapor from commercial, un-dried MeOH also produces a green emission with incorporation of $H_2O$; however, removal of the incorporated water by acetonitrile or vacuum takes more time or gentle warming.

Thus, as demonstrated by the foregoing, according to another embodiment of the invention, the method of detecting an analyte may further comprise regenerating the first complex by exposing the second complex with the heteroatom-containing ligand of the first complex. In one example, complex 2b may be treated with acetonitrile to regenerate complex 1b. Alternatively or additionally, the method may include subjecting the second complex to a reduced pressure atmosphere to thereby remove the analyte from the second complex to form a third complex; and regenerating the first complex by exposing the third complex with the heteroatom-containing ligand of the first complex. For example, complex 2b may be subject to vacuum treatment, which is then followed by treatment with gaseous acetonitrile in nitrogen.

Figure 10:
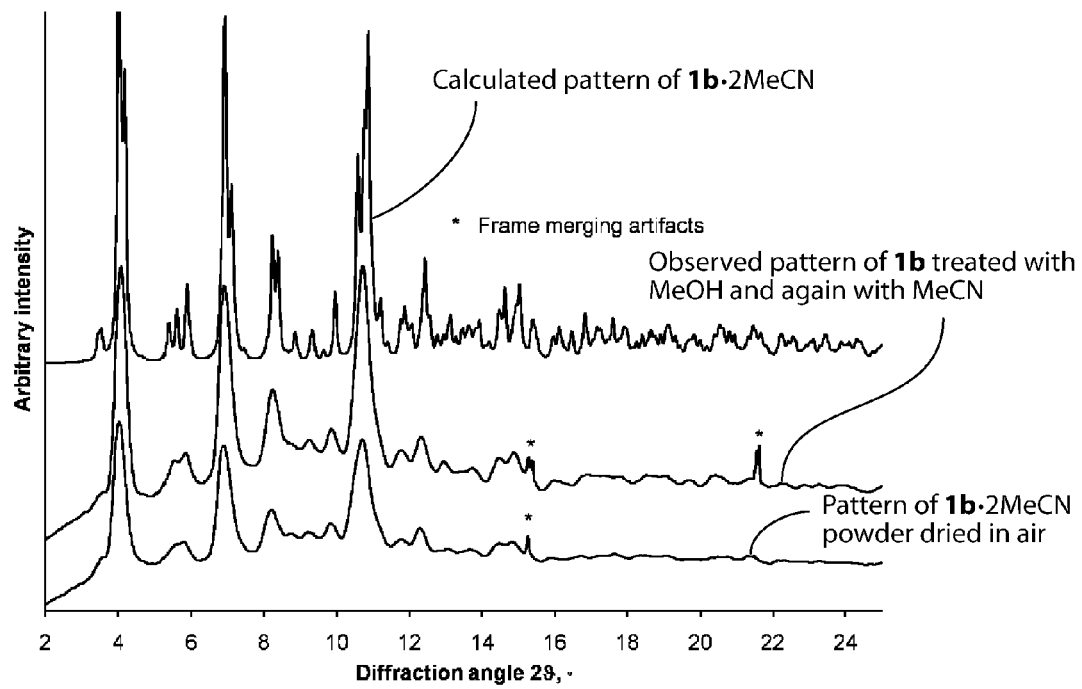
FIG. 10 is an X-ray powder diffraction patterns of complex 1b stacked for ease of comparison.

FIGS. 10 and 11 show X-ray powder diffractrograms of complexes 1b and 2b after various processing steps. The X-ray powder pattern obtained from a dry sample of complex 1b and the one calculated from the crystal structure of complex 1b.2MeCN agree closely thus demonstrating that loss of MeCN does not significantly change the crystal structure, and crystallinity is preserved. When a MeOH-exposed sample was treated with MeCN vapor, the blue luminescence was restored, and the powder XRD pattern showed the same structure as the original sample (FIG. 10), thus proving the reversibility of the reaction and the ability to recover the original structure of complex 1b.2MeCN. On the other hand, drying complex 2b.2MeOH.2Et$_2$O produces a different X-ray diffraction pattern as compared to the one calculated from the crystal structure of complex 2b.2MeOH.2Et$_2$O, which showed that loss of solvent in this complex leads to a different crystal structure. Both X-ray powder diffraction patterns of dried crystals of complex 2b.2MeOH.2Et$_2$O and complex 1b treated with dry MeOH vapor were identical (FIG. 11). This result shows that only one product, complex 2b, is formed both homogeneously by dissolving complex 1b in MeOH followed by crystallization as well as heterogeneously by the action of MeOH vapor on complex 1b.

Additionally, another exemplary analyte is acetone (Me$_2$CO). Treatment of complex 1b with Me$_2$CO vapor changes the solid-state luminescence color from blue to yellow-orange ($\lambda_{max}$=591 nm), a maximum wavelength distinct from the evacuated MeOH$_{(g)}$ sample indicating the presence of a different species. This luminescence change can also be brought about by a quantity of Me$_2$CO$_{(l)}$ insufficient to dissolve all the compound. In one example, the $^1$H and $^{13}$C{$^1$H} NMR analyses showed the presence of both Me$_2$CO (0.8-1 eq eq.) and residual MeCN (0.1 eq.) in the converted sample, but residual MeCN can be effectively eliminated by increasing the duration of the exposure thereby permitting the conversion to run to completion. However, the structural make-up of this species has yet to be determined.

Complexes 1b and 2b exhibit reversible luminescent vapochromic behavior through ligand exchange reactions allowing the sensing of MeCN, H$_2$O, MeOH, Me$_2$CO, and the like vapors. The interchange between MeCN and MeOH exposure induces a profound change in Au—Cu bonding depending on the coordination number at the copper centers.

As will be appreciated by a person skilled in the art, the vapochromic gold-copper complexes of the invention may find application in a wide range of industrial and commercial applications, such as in the chemical, energy and environmental sectors. The vapochromic gold-copper complexes may be used in many different solid forms depending upon the vapochromic application, such as powders, crystals, thin films or combinations thereof. Exemplary industrial applications include: personal and badge monitors in chemical laboratories (e.g. industrial chemical or pharmaceutical research laboratories, paint and coatings manufacturing, cosmetics manufacturing) for hazardous vapor detection; portable or stationary threshold monitors for chemical vapors in laboratory environments or chemical storage facilities for hazardous vapor detection or regulated emission requirements; environmental sensor for volatile organic compounds or gases ("electronic noses") for use at environmental remediation sites, landfills, air-quality monitoring etc.; application to the area of biofuels, where fermentation would produce MeOH as a liquid fuel for transportation or fuel cells; and responsive coatings, art supplies, color-changing paint and other related applications where a color-changing material is desired.

As will be apparent to a person skilled in the art, the vapochromic gold-copper complexes described herein may be deployed in various different forms and applications for specifically detecting alcohols, ketones, aldehydes, etc. For example, the vapochromic gold-copper complexes may be used in medical applications for sensing alcohols, ketones, or aldehydes in the breath of patients. In one embodiment, a vapochromic gold-copper complex may be embedded in a paper strip, similar to litmus paper, or onto a binding agent such as silica, which a patient would be instructed to breathe on.

As discussed herein, the products obtained by treating a vapochromic gold-copper complex, such as complex 1b, with solvent vapors have been characterized by their luminescence (FIGS. 2-9); powder X-ray diffraction (FIGS. 10-11) spectra; $^1$H and $^{13}$C{$^1$H} NMR (FIGS. 12-15), and/or IR (see data of specific compound).

EXPERIMENTAL

General Instrumentation

NMR spectra were recorded at 25° C. on Varian NMR System 500 or Varian 400-MR spectrometers at the indicated frequency and were referenced relative to TMS. Assignments were based upon interpretation of gcosy and ghsqc experiments. Deuterated solvents were deoxygenized by two freeze-thawing cycles. Solid-state fluorescence spectra were recorded on a Jobin Yvon Horiba FluoroMax-3 instrument. No special precautions were necessary to guard against air or moisture except for the spectrum of complex 1b exposed to dry MeOH vapor which was measured in a vessel suitable for evacuation. Mass spectroscopy was conducted on a Waters micromass ZQ instrument using electrospray ionization in positive ion mode. IR spectra were recorded at 2 cm$^{-1}$ resolution on a Thermo Nicolet 6700 FT-IR instrument equipped with a ZnSe ATR accessory. Elemental analyses were performed by Midwestlab, Indianapolis. Photographs were taken with an Olympus FE-100 digital camera and are shown without further processing. Samples in pictures and during titration experiments were excited at 365 nm using a handheld UVP UVGL-25 lamp.

Single-crystal and powder X-ray diffraction was performed on a Bruker SMART Apex CCD instrument at 100 K using graphite-monochromated Mo K$_\alpha$ radiation, crystals were immersed in Paratone oil and mounted on glass fibers, powders were picked up on glass fibers with a drop of Paratone oil. Data were corrected for Lorentz and polarization effects using the SAINT program and corrected for absorption using SADABS. The structures were solved by Patterson syntheses using the SHELXTL 6.10 software package. Mercury 2.3 was used to calculate powder diffraction spectra from crystal structure CIFs.

Final refinement of the crystal and molecular structure of complex 2b was performed with restraints on the O—H bond length of the coordinated MeOH [0.84(1) Å] as well as its H . . . O distance to the oxygen atom of the lattice methanol [1.75(10) Å]. Due to these restraints the s.u. values of the respective bonds reported in the CIF file are too small and meaningless. P—F bonds in the rotationally disordered $PF_6^-$ anion containing P2 as well as the C—C bonds in $Et_2O$ were restrained to be of equal length. Table 1 below summarizes data and parameters of the structures presented.

Tetrakis(acetonitrile-1κ(N))bis{$\eta^3$-$\mu_3$-1,3-bis[(2-pyridyl-1κN)methyl]-2H-imidazol-2-ylidene-2κC}dicopper(I)gold(I)tris(hexafluorophosphate) (1b)

In a Schlenk flask 50 mL acetonitrile was deoxygenized by two freeze-thawing cycles. $[Au(im(CH_2py)_2)_2]PF_6$ (200.9 mg, 238 μmol) and $[Cu(MeCN)_4]PF_6$ (180.6 mg, 485 μmol, 2 eq.) were added and the clear solution stirred for 2 h. The solution was then reduced to 25 mL and layered with 50 ml of diethyl ether that was similarly deoxygenized. The Schlenk flask was left at −10° C. for 6 days whereupon few crystals of the acetonitrile disolvate were taken for X-ray diffraction, the

TABLE 1

Crystallographic data and parameters.

| Compound | 1•2MeCN | 2•2MeOH•2Et$_2$O | 6 |
|---|---|---|---|
| Formula | C$_{38}$H$_{40}$AuCu$_2$F$_{18}$N$_{12}$P$_3$•2C$_2$H$_3$N | C$_{32}$H$_{36}$AuCu$_2$F$_{18}$N$_8$O$_2$P$_3$•2CH$_4$O•2C$_4$H$_{10}$O | C$_{38}$H$_{44}$AuCu$_2$F$_{18}$N$_8$P$_3$S$_2$ |
| FW | 1505.9 | 1536.0 | 1435.89 |
| Crystal morphology and size, mm | Colorless prism, 0.14 × 0.10 × 0.06 | Colorless needle, 0.17 × 0.04 × 0.03 | Colorless shard, 0.24 × 0.12 × 0.04 |
| Crystal system | Monoclinic | Orthorhombic | Triclinic |
| Space group | P2$_1$/m (No. 11) | Pbcn (No. 56) | P-1 (No. 2) |
| a, Å | 11.9958(2) | 10.9774(4) | 10.8005(4) |
| b, Å | 19.8135(5) | 19.1174(6) | 10.8767(4) |
| c, Å | 12.3023(2) | 27.1633(10) | 11.5095(5) |
| β, ° | 106.354(1) | 90 | 95.1330(10) |
| V, Å$^3$ | 2805.69(10) | 5700.5(3) | 96.5480(10) |
| Z | 2 | 4 | 1 |
| ρ, Mg·m$^{-3}$ | 1.783 | 1.790 | 1.930 |
| μ, mm$^{-1}$ | 3.550 | 3.501 | 4.104 |
| R$_1$ [I > 2σ(I)] | 0.0410 | 0.0388 | 0.0192 |
| wR$_2$ (all data) | 0.1104 | 0.0964 | 0.0465 |

Vapor Experiments

Powdered samples of complex 1b were spread out on a watch glass or put into vials and placed under a vacuum bell equipped with a vapor inlet designed to direct the gas stream onto the sample or into the vial. A filter flask was used to generate solvent vapor by passing $N_2$ through the solvent. For experiments under exclusion of moisture, $N_2$ was pre-dried with $CaCl_2$ before bubbling into solvents which contained suspended $MgSO_4$ and $CuSO_4$. Contact of complex 1b with the glass surface was found to accelerate the reaction. The progress of the conversion was monitored by fluorescence spectroscopy and NMR, and once found to be complete, the powder was additionally analyzed by NMR and IR spectroscopy.

Preparation of Compounds $[Cu(MeCN)_4]PF_6$, $[im(CH_2py)_2]PF_6$ (using 1-propanol instead of EtOH), [AuCl(tht)] (tht=tetrahydrothiophene) and $[Au\{im(CH_2py)_2\}_2]PF_6$ were prepared according to the literature methods (e.g., Kubas, G. J. Inorg. Synth. 1990, 28, 68-70; Magill, A. M.; McGuinness, D. S.; Cavell, K. J.; Britovsek, G. J. P.; Gibson, V. C.; White, A. J. P.; Williams, D. J.; White, A. H.; Skelton, B. W. J. Organomet. Chem. 2001, 617-618, 546-560; Usón, R.; Laguna, A.; Laguna, M. Inorg. Synth. 1989, 26, 85-91; and Catalano, V. J.; Malwitz, M. A.; Etogo, A. O. Inorg. Chem. 2004, 43, 5714-5724, respectively, each of which is incorporated herein in its entirety). Syntheses were performed utilizing standard Schlenk techniques under an atmosphere of $N_2$. MeCN and $CH_2Cl_2$ were dried by passing through a column of alumina, anhydrous $Et_2O$, HPLC grade MeOH, 2-(chloromethyl)pyridinium hydrochloride, imidazole, $KPF_6$, 60% aqueous $HPF_6$, $H[AuCl_4]$·$4H_2O$, $Cu_2O$ and tetrahydrothiophene (tht) were used as received.

rest was isolated and dried in vacuo affording complex 1b free of lattice solvent. Yield 261 mg (77%) of a tan powder soluble in MeCN and $Me_2CO$; soluble in hot MeOH forming complex 2b. The complex is very stable to air as a solid and in MeCN solutions, stability in ketone solvents is limited, and oxidation to Cu$^{II}$ species occurs. $^1$H NMR [499.8 MHz, $(CD_3)_2CO$, ppm]: δ8.85 (d, 4H, $^3$J=5.05 Hz, H$^6$ py), 8.24 (td, 4H, $^3$J=7.8 Hz, $^4$J=1.0 Hz, H$^4$ py), 8.02 (d, 4H, $^3$J=7.8, H$^3$ py), 7.87 (s, 4H, CH imidazole), 7.70 (m, 4H, H$^5$ py), 5.98 (s, 8H, CH$_2$), 2.07 (s, 12H, MeCN). $^{13}$C{$^1$H} NMR [125.7 MHz, $(CD_3)_2CO$, ppm]: δ181.0 (CAu), 155.3 (C$^2$py), 152.1 (C$^6$ py), 141.7 (C$^4$ py), 127.5 (C$^3$ py), 126.8 (CH imidazole), 124.7 (C$^5$ py), 117.8 (CH$_3$CN), 57.6 (CH$_2$), 1.2 (CH$_3$CN). MS (ESI+, $Me_2CO$ solution, m/z): 779 (L$_2$AuCuF$^+$, 1%), 759 [(L$_2$AuCu—H)$^+$, 4%], 697 (L$_2$Au$^+$, 100%). IR (ATR, cm$^{-1}$): 2310w (vCN), 2276w (v CN), 2252vw (v CN), 1603m (v ar C═C), 837vs ($v_{as}$ PF$_6^-$). Anal. Calcd (%) for C$_{38}$H$_{40}$AuCu$_2$F$_{18}$N$_{12}$P$_3$: C 32.05, H 2.83, N 11.81; found: C 32.43, H 3.01, N 11.50.

Bis $\eta^3$-$\mu_3$-1,3-bis[(2-pyridyl-1κN)methyl]-2H-imidazol-2-ylidene-2κC}bis(methanol-1κO)dicopper(I) gold(I)2(Au—Cu)tris(hexafluorophosphate) (2b)

A Schlenk flask was charged with 40 mL deoxygenized methanol and complex 1b (100 mg, 75 μmol). The complex dissolved upon heating to 60° C. Once cooled to 20° C. the homogeneous solution was layered with an equal volume of diethyl ether and left to crystallize at 20° C. Dried yield 56 mg (44 mmol, 59% according to NMR stoichiometry) of colorless crystals soluble in acetone and less soluble in methanol. The complex is stable to air as a solid and fairly stable in MeOH solution eventually depositing Cu$^{II}$ oxidation products over the course of days. $^1$H NMR [499.8 MHz, (CD$_3$)$_2$CO, ppm]: δ8.89 (m, 4H, H$^6$ py), 8.26 (m, 4H, H$^4$ py), 8.05 (m, 4H, H$^3$ py), 7.88 (s, 4H, CH imidazole), 7.73 (m, 4H, H$^5$ py), 6.00 (s, 8H, pyCH$_2$), 3.41 (q, 2.7H, $^3$J=7.0 Hz, CH$_3$CH$_2$O), 3.31 (m, 1.5H, CH$_3$OH), 3.07 (q, 0.3H, CH$_3$OH, $^3$J=5.4 Hz), 1.11 (t, 4H, $^3$J=7.0 Hz, CH$_3$CH$_2$O). $^{13}$C{$^1$H} NMR [125.7 MHz, (CD$_3$)$_2$CO, ppm]: δ157.5 (C$^2$ py), 154.5 (C$^6$ py), 144.4 (C$^4$ py), 130.5 (C$^3$ py), 129.6 (C$^5$ py), 127.4 (CH imidazole), 70.1 (CH$_3$CH$_2$O), 61.9 (pyCH$_2$), 20.7 (CH$_3$CH$_2$O). $^{13}$C signals for carbene and MeOH carbon atoms were not observed. IR (ATR, cm$^{-1}$): 3647w (ν OH), 3566w (ν OH), 1610m (ν ar C=C), 835vs (ν$_{as}$ PF$_6^-$). MS (ESI+, MeOH solution, m/z): 447.55 (LAu$^+$, 20%), 697.76 (L$_2$Au$^+$, 20), 313.32 (LCu$^+$, 100). Anal. Calcd (%) for C$_{32}$H$_{36}$AuCu$_2$F$_{18}$N$_8$O$_2$P$_3$.0.5C$_4$H$_{10}$O: C 30.01, H 3.04, N 8.24; found: C 30.10, H 2.90, N 7.93.

Bis{η$^3$-μ$_3$-1,3-bis[(2-pyridyl-1κN)methyl]-2H-imidazol-2-ylidene-2κC}tetrakis(acetonitrile-1κN)dicopper(I)gold(I)tris(hexafluorophosphate) (1b)

A Schlenk tube was charged with 50 mL of MeCN and the solvent was degassed by two freeze-thaw cycles. [Au(im(CH$_2$py)$_2$)$_2$]PF$_6$ (200.9 mg, 0.238 mmol) and [Cu(MeCN)$_4$]PF$_6$ (180.6 mg, 0.485 mmol) were added and the product precipitated by 75 mL diethyl ether, which had been deoxygenized by passing N$_2$ through the solvent. Yield 261 mg (77%). $^1$H NMR [499.8 MHz, (CD$_3$)$_2$CO, 25° C.] δ8.85 (m, 4H, H-6 py), 8.24 (td, $^3$J=7.8 Hz, $^4$J=1.0 Hz, 4H, H-4 py), 8.02 (m, 4H, H-3 py), 7.87 (s, 4H, H-4/5 im), 7.70 (m, 4H, H-5 py), 5.98 (s, 8H, CH$_2$), 2.07 (s, 12H, CH$_3$CN). $^{13}$C{$^1$H} NMR [125.7 MHz, CD$_3$CN, 25° C.] δ 181.0, 155.3, 152.1, 141.7, 127.5, 126.8, 124.7, 117.8, 57.6, 1.2. MS (ESI$^+$) m/z 779 [Au(im(CH$_2$py)$_2$)$_2$CuF]$^+$, 759 [[Au(im(CH$_2$py)$_2$)$_2$Cu]—H]$^+$, 697 [Au(im(CH$_2$py)$_2$)$_2$]$^+$. Anal. Calcd (%) for C$_{38}$H$_{40}$AuCu$_2$F$_{18}$N$_{12}$P$_3$: C 32.05, H 2.83, N 11.81; found: C 32.43, H 3.01, N 11.50. The unit cell dimensions of crystals grown from acetonitrile/diethyl ether are a, 119.958(2) nm; b, 198.135(5) nm; c, 123.023(2) nm; α, 90°; β, 106.354(1)°; γ, 90° (monoclinic primitive crystal system). Crystallization from acetone/diethyl ether affords crystals with the unit cell dimensions a, 146.938(3) nm; b, 202.955(4) nm; c, 121.932 (3) nm; α, 90°; β, 126.942(1)°; γ, 90° (monoclinic centered crystal system). Luminescence λ$_{max}$ 462 nm.

ADDITIONAL EXAMPLES

Additional examples of complexes with various anions were also prepared. Preparation of the starting materials with different anions largely follows the published procedures for [Cu(CH$_3$CN)$_4$]PF$_6$ and [Au(im(CH$_2$py)$_2$)$_2$]BF$_4$ (see FIG. 1, Kubas, G. J. *Inorg. Synth.* 1990, 28, 68-70; and Catalano, V. J.; Malwitz, M. A.; Etogo, A. O. *Inorg. Chem.* 2004, 43, 5714-5724, each of which is incorporated by reference herein in its entirety). The procedure must however be modified for the SbF$_6$ anion, which is not stable to caustics. The silver complex [Ag(im(CH$_2$py)$_2$)$_2$]Cl is prepared and the chloride anion is exchanged for hexafluoroantimonate(V), affording [Ag(im(CH$_2$py)$_2$)$_2$]SbF$_6$, which is used to prepare the analogous gold complex, [Au(im(CH$_2$py)$_2$)$_2$]SbF$_6$ (see Catalano, V. J.; Malwitz, M. A. *Inorg. Chem.* 2003, 42, 5483-5485, which is incorporated herein by reference in its entirety). The trinuclear gold dicopper complexes are then prepared by mixing one equivalent of [Au(im(CH$_2$py)$_2$)$_2$]X, dissolved in deoxygenized acetonitrile and 2 equivalents of [Cu(CH$_3$CN)$_4$]X (see Strasser, C. E.; Catalano, V. J. *J. Am. Chem. Soc.* 2010, 132, 10009-10011, which is incorporated herein by reference in its entirety). Once a homogeneous solution is obtained, the products were precipitated with diethyl ether and isolated in 70-95% yield or obtained in a crystalline state by layering the acetonitrile solution with diethyl ether. After drying the products, they are characterized by appropriate techniques to ensure a ligand-to-acetonitrile ratio of 2:4. A word of caution: perchlorate salts are potentially explosive and should be handled carefully and in small quantities.

Bis{η$^3$-μ$_3$-1,3-bis[(2-pyridyl-1κN)methyl]-2H-imidazol-2-ylidene-2κC}tetrakis(acetonitrile-1κN)dicopper(I)gold(I)tris(perchlorate) (1c)

The complex was prepared adding [Au(im(CH$_2$py)$_2$)$_2$]ClO$_4$ (160.8 mg, 0.202 mmol), [Cu(MeCN)$_4$]ClO$_4$ (132.9 mg, 0.406 mmol) to 20 mL CH$_3$CN that was degassed by two freeze-thaw cycles. Addition of 50 mL diethyl ether, which had been deoxygenized by passing N$_2$ through the solvent precipitated a colorless powder (244 mg, 94.0%). $^1$H NMR [499.8 MHz, (CD$_3$)$_2$CO, 25° C.] δ8.79 (m, 4H, H-6 py), 8.15 (td, $^3$J=7.7 Hz, $^4$J=1.5 Hz, 4H, H-4 py), 7.91 (m, 4H, H-3 py), 7.78 (s, 4H, H-4/5 im), 7.63 (m, 4H, H-5 py), 5.89 (s, 8H, CH$_2$), 2.04 (s, 12H, CH$_3$CN). The powder obtained was further characterized by powder diffraction affording a pattern similar to complex 1d. Luminescence λ$_{max}$ 460 nm.

Bis η$^3$-μ$_3$-1,3-bis[(2-pyridyl-1κN)methyl]-2H-imidazol-2-ylidene-2κC}tetrakis(acetonitrile-1κN)dicopper(I)gold(I)tris(tetrafluoroborate) (1d)

A Schlenk tube was charged with 25 mL of MeCN and the solvent was degassed by two freeze-thaw cycles. [Au(im(CH$_2$py)$_2$)$_2$]BF$_4$ (152.6 mg, 194 μmol) and [Cu(MeCN)$_4$]BF$_4$ (123.2 mg, 392 μmol) were added and stirred for 1 h. Addition of 75 mL Et$_2$O deoxygenized by passing N$_2$ through the solvent precipitated a colorless solid that was isolated by filterstick filtration. Yield 190 mg (78.6%). The complex is soluble in MeCN, Me$_2$CO and also in MeOH. $^1$H NMR [399.9 MHz, (CD$_3$)$_2$CO, 25° C.] δ8.86 (m, 4H, H-6 py), 8.24 (td, $^3$J=7.8 Hz, $^4$J=1.7 Hz, 4H, H-4 py), 8.08 (m, 4H, H-3 py), 7.88 (s, 4H, H-4/5 im), 7.71 (m, 4H, H-5 py), 5.98 (s, 8H, CH$_2$), 2.09 (s, 12H, CH$_3$CN). $^{13}$C{$^1$H} NMR [100.5 MHz, CD$_3$CN, 25° C.] δ156.4, 153.2, 142.9, 128.8, 127.9, 125.8, 58.6, 2.3. $^{19}$F{$^1$H} NMR (376.3 MHz, (CD$_3$)$_2$CO, 25° C.) δ −150.9 ($^{10}$BF$_4$), −151.0 ($^{11}$BF$_4$). MS (ESI$^+$) m/z 846.1449 (C$_{30}$H$_{28}$AuBCuF$_4$N$_8^+$ requires 846.1459). The unit cell dimensions of crystals grown from acetonitrile/diethyl ether are a, 145.248(2) nm; b, 192.511(3) nm; c, 117.453(3) nm; α, 90°; β, 126.411°; γ, 90° (monoclinic centered crystal system). Luminescence λ$_{max}$ 462 nm.

Bis{η$^3$-μ$_3$-1,3-bis[(2-pyridyl-1κN)methyl]-2H-imidazol-2-ylidene-2κC}tetrakis(acetonitrile-1κN)dicopper(I)gold(I)tris[hexafluoroarsenate(V)] (1e)

The complex was prepared by adding [Au(im(CH$_2$py)$_2$)$_2$]AsF$_6$ (400 mg, 0.451 mmol) to [Cu(MeCN)$_4$]AsF$_6$ (376 mg, 0.902 mmol) in 20 mL MeCN that was degassed by two freeze-thaw cycles. Addition of 90 mL Et$_2$O deoxygenized by passing N$_2$ through the solvent precipitated a colorless powder (649 mg, 92.5%). $^1$H NMR [499.8 MHz, (CD$_3$)$_2$CO, 25° C.] δ8.85 (m, 4H, H-6 py), 8.26 (td, $^3$J=7.8 Hz, $^4$J=1.6 Hz, 4H, H-4 py), 8.04 (m, 4H, H-3 py), 7.89 (s, 4H, H-4/5 im), 7.72 (m, 4H, H-5 py), 6.00 (s, 8H, CH$_2$), 2.10 (s, 12H, CH$_3$CN). $^{13}$C{$^1$H} NMR [125.7 MHz, CD$_3$CN, 25° C.] δ177.8, 152.7, 149.6, 139.6, 125.7, 125.0, 122.8, 116.2, 65.4, 2.0. $^{19}$F{$^1$H} NMR [376.3 MHz, (CD$_3$)$_2$CO, 25° C.] δ−65.4 (1:1:1:1-q, $^1J_{AsF}$ 917 Hz). MS (ESI$^+$) m/z 949.0519 ($C_{30}H_{28}AsAuF_6N_8^+$ requires 949.0513). The unit cell dimensions of crystals grown from acetonitrile/diethyl ether are a, 200.825(4) nm; b, 149.621(3) nm; c, 214.263(4) nm; α, 90°; β, 90°; γ90° (orhorhombic centered crystal system). Luminescence $\lambda_{max}$ 460 nm.

Bis{η$^3$-µ$_3$-1,3-bis[(2-pyridyl-1κN)methyl]-2H-imidazol-2-ylidene-2κC}tetrakis(acetonitrile-1κN)dicopper(I)gold(I)tris[hex afluoroantimonate(V)] (1f)

The complex was prepared adding [Au(im(CH$_2$py)$_2$)$_2$]SbF$_6$ (380.4 mg, 0.408 mmol), [Cu(MeCN)$_4$]SbF$_6$ (379 mg, 0.818 mmol) to 25 mL CH$_3$CN that was degassed by two freeze-thaw cycles. Addition of 75 mL diethyl ether deoxygenized by passing N$_2$ through the solvent precipitated a colorless powder (515 mg, 74.5%). $^1$H NMR [499.8 MHz, (CD$_3$)$_2$CO, 25° C.] δ8.86 (m, 4H, H-6 py), 8.25 (td, $^3$J=7.8 Hz, $^4$J=1.8 Hz, 4H, H-4 py), 8.05 (m, 4H, H-3 py), 7.89 (s, 4H, H-4/5 im), 7.72 (m, 4H, H-5 py), 6.00 (s, 8H, CH$_2$), 2.10 (s, 12H, CH$_3$CN). $^{13}$C{$^1$H} NMR [125.7 MHz, CD$_3$CN, 25° C.] δ177.6, 152.7, 149.7, 139.6, 125.8, 124.9, 122.8, 116.2, 65.4, 2.0. The unit cell dimensions of crystals grown from acetonitrile/diethyl ether are a, 205.872(3) nm; b, 150.112(2) nm; c, 217.271(3) nm; α, 90°; β, 90°; γ, 90° (orhorhombic centered crystal system). Luminescence $\lambda_{max}$ 483 nm.

Complex 1B Treated with Dry MeOH Vapor.
$^1$H NMR [499.8 MHz, (CD$_3$)$_2$CO, ppm]: δ8.89 (m, 4H, H$^6$ py), 8.26 (m, 4H, H$^4$ py), 8.04 (m, 4H, H$^3$ py), 7.88 (s, 4H, CH imidazole), 7.72 (m, 4H, H$^5$ py), 6.00 (s, 8H, CH$_2$), 3.32 (d, 2.1H, $^3$J=5.4 Hz, CH$_3$OH), 3.30 (s, 2.5H, CH$_3$OH), 3.09 (q, 0.9H, $^3$J=5.4 Hz, CH$_3$OH), 2.79 (s, 1H, CH$_3$OH+H$_2$O). $^{13}$C{$^1$H} NMR [125.7 MHz, (CD$_3$)$_2$CO, ppm]: δ155.4, 152.3, 142.0, 127.8, 126.9, 124.7, 57.7. $^{13}$C NMR signals due to the carbene carbon and MeOH were not observed. IR (ATR, cm$^{-1}$): 3649w (ν OH), 3564w (ν OH), 3180w (ν ar CH), 3155w (ν ar CH), 3124w (ν ar CH), 1610m (ν ar C=C), 834vs ($ν_{as}$ PF$_6^-$).

Complex 1B Treated with Dry MeOH Vapor and Exposed to the Atmosphere.
$^1$H NMR [499.8 MHz, (CD$_3$)$_2$CO, ppm]: δ8.84 (m, 4H, H$^6$ py), 8.21 (m, 4H, H$^4$ py), 7.98 (m, 4H, H$^3$ py), 7.83 (m, 4H, CH imidazole), 7.68 (m, 4H, H$^5$ py), 5.96 (s, 8H, CH$_2$), 3.03 (s, 2.2H, CH$_3$OH), 2.82 (s, 2.8H, CH$_3$OH+H$_2$O). IR (ATR, cm$^{-1}$): 3649m (ν OH), 3565w (νOH), 3178w (ν ar CH), 3154w (ν ar CH), 3121 (ν ar CH), 1610m (ν ar C=C), 834vs ($ν_{as}$ PF$_6^-$). The IR spectrum is identical to the spectrum before exposition to the atmosphere but for the higher intensity of the 3649 cm$^{-1}$ band.

Complex 1B Treated with Dry MeOH Vapor and Evacuated.
$^1$H NMR [499.8 MHz, (CD$_3$)$_2$CO, ppm]: δ8.79 (m, 4H, H$^6$ py), 8.15 (m, 4H, H$^4$ py), 7.89 (m, 4H, H$^3$ py), 7.78 (s, 4H, CH imidazole), 7.62 (m, 4H, H$^5$ py), 5.91 (s, 8H, CH$_2$).

Complex 1B Treated with Me$_2$CO Vapor
$^1$H NMR [499.8 MHz, CD$_3$OD/(CD$_3$)$_2$SO 7:2, ppm]: δ8.67 (m, 4H), 7.97 (m, 4H), 7.59 (s, 4H), 7.49 (s, 4H), 5.67 (s, 8H), 2.17 (s, 5.4H, Me$_2$CO), 2.07 (0.3H, MeCN). IR (ATR, cm$^{-1}$): 1706m (ν CO), 1610m (ν ar), 1367w ($ν_{sy}$ CH$_3$), 847vs ($ν_{as}$ PF$_6^-$), 832vs ($ν_{as}$ PF$_6^-$).

Complex 1B Treated with Tetrahydrothiophene in Solution
Complex 1b as prepared above and free of lattice solvent (100 mg, 75.5 µmol) was dissolved in a minimum amount of acetone (15 mL). An excess of tetrahydrothiophene (about 0.5 mL, 5.6 mmol) was then added carefully via syringe. The homogeneous mixture was stirred for 0.5 h whereupon diethyl ether was layered on top of the solution. Crystallization at 23° C. produced X-ray quality crystals of the tetrahydrothiophene complex. The X-ray crystollaphic data of the tetrahydrothiophene complex 6 is provided in Table 1 above. Unit cell dimensions (triclinic primitive system): a, 108.005 (4) nm; b, 108.767(4) nm; c, 115.095(5) nm; α, 95.133(1)°; β, 96.548(1)°; γ, 111.686(1)°. The complex is unstable in solution, and the tetrahydrothiophene ligands dissociate.

While the invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and/or method and examples shown and described. The various features of exemplary embodiments described herein may be used in any combination. Accordingly, departures may be made from such details without departing from the scope of the general inventive concept.

What is claimed is:

1. A vapochromic gold-copper complex of a general formula

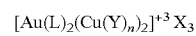

in which L is an N-heterocyclic carbene; Y is a heteroatom-containing ligand; X is an anion, and n is an integer having a value of 1 or 2, and solvates thereof.

2. The complex of claim 1, wherein the N-heterocyclic carbene is of the general formula

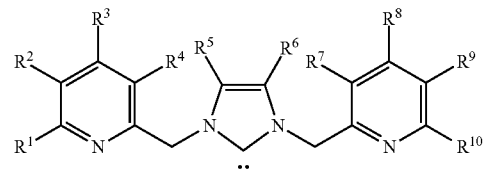

wherein R$^1$ though R$^{10}$ are independently selected from hydrogen, an alkyl, aryl, alkaryl, alkenyl, cycloalkyl, heteroalkyl, heteroaryl, or a halide.

3. The complex of claim 2, wherein R$^1$ through R$^{10}$ are each hydrogen.

4. The complex of claim 1, wherein the anion is a weakly or non-coordinating anion.

5. The complex of claim 1, wherein the anion is selected from PF$_6^-$, BF$_4^-$, AsF$_6^-$, SbF$_6^-$, or ClO$_4^-$.

6. The complex of claim 1, wherein the heteroatom-containing ligand is selected from water, an alcohol, a nitrile, a ketone, an aldehyde, a carboxylic ester, a carbonic ester, a thioether, an amine, an imine, a phosphonic ester, a phosphoric ester, or a phosphorous ester.

7. The complex of claim 1, wherein the heteroatom-containing ligand is an organic compound selected from the group consisting of methanol, ethanol, acetone, methyl ethyl ketone, tetrahydrothiophene, dimethylsulfide, acetonitrile, and a phosphorus-containing compound.

8. The complex of claim 1 having the chemical formula:

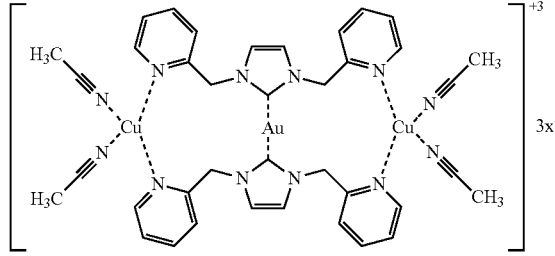

wherein X is an anion selected from the group consisting of $PF_6^-$, $BF_4^-$, $AsF_6^-$, $SbF_6^-$, or $ClO_4^-$.

9. A chemical sensor device comprising the complex of claim 1.

10. A method of detecting an analyte comprising:
(a) exposing a first complex to the analyte, wherein the first complex is a vapochromic gold-copper complex having the general formula of claim 1, and
wherein the first complex is reversibly transformed to a second complex by replacement of at least one of the heteroatom-containing ligands by the analyte upon exposing the first complex to the analyte; and
(b) observing a photoluminescent or infrared absorbance change in the second complex relative to the first complex resulting from exposure to the analyte.

11. The method of claim 10, wherein the analyte is selected from water, an alcohol, a nitrile, a ketone, an aldehyde, a carboxylic ester, a carbonic ester, a thioether, an amine, an imine, a phosphonic ester, a phosphoric ester, or a phosphorous ester.

12. The method of claim 10, wherein the analyte is an organic compound selected from the group consisting of methanol, ethanol, acetone, methyl ethyl ketone, tetrahydrothiophene, dimethylsulfide, acetonitrile, and a phosphorus-containing compound.

13. The method of claim 10, wherein the N-heterocyclic carbene is of the general formula

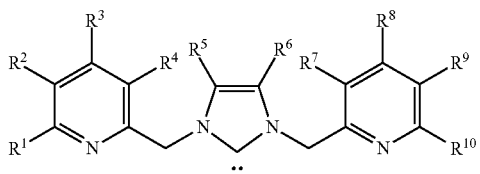

wherein $R^1$ though $R^{10}$ are independently selected from hydrogen, an alkyl, aryl, alkaryl, alkenyl, cycloalkyl, heteroalkyl, heteroaryl, or a halide.

14. The method of claim 13, wherein $R^1$ though $R^{10}$ are hydrogen.

15. The method of claim 10, wherein the first complex is of the chemical formula:

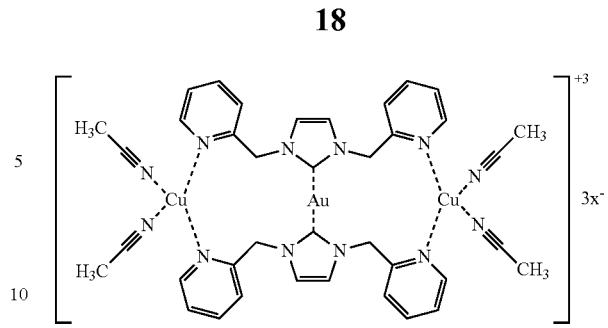

wherein X is an anion selected from the group consisting of $PF_6^-$, $BF_4^-$, $AsF_6^-$, $SbF_6^-$, or $ClO_4^-$.

16. The method of claim 10, further comprising:
regenerating the first complex by exposing the second complex to the heteroatom-containing ligand of the first complex.

17. The method of claim 10, further comprising:
subjecting the second complex to a reduced pressure atmosphere to thereby remove the analyte from the second complex to form a third complex; and
regenerating the first complex by exposing the third complex to the heteroatom-containing ligand of the first complex.

18. A method of making a complex having the general formula
of claim 1, the method comprising:
reacting the N-heterocyclic carbene with a silver salt to form a bis-N-heterocyclic carbene silver compound in a first solvent;
forming a bis-N-heterocyclic carbene gold complex by reacting the bis-N-heterocyclic carbene silver complex with a gold compound in a second solvent; and
forming the complex by reacting the bis-N-heterocyclic carbene gold complex with a copper compound in a third solvent, wherein the first, second, and third solvents may be the same or different.

19. The method of claim 18, wherein the third solvent is the heteroatom-containing ligand.

20. The method of claim 18, wherein the complex is of the chemical formula:

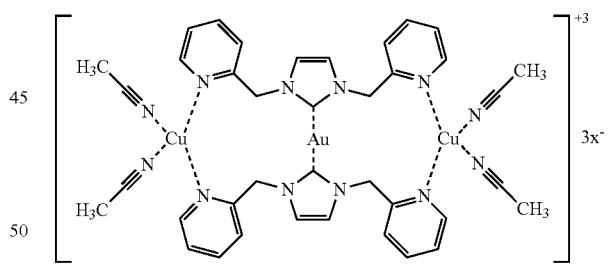

wherein X is an anion selected from the group consisting of $PF_6^-$, $BF_4^-$, $AsF_6^-$, $SbF_6^-$, or $ClO_4^-$.

21. The method of claim 20, wherein the third solvent is acetonitrile.

22. The complex of claim 1, wherein the complex has a formula

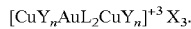

[$CuY_nAuL_2CuY_n$]$^{+3}$ $X_3$.

23. The complex of claim 1, wherein the complex has a formula

[$Cu(CH_3CN)AuL_2Cu(CH_3CN)$]$^{+3}$ $X_3$.

* * * * *